(12) United States Patent
Kamatani et al.

(10) Patent No.: US 7,927,718 B2
(45) Date of Patent: Apr. 19, 2011

(54) COMPOUND FOR ORGANIC EL DEVICE AND LIGHT-EMITTING DEVICE

(75) Inventors: Jun Kamatani, Tokyo (JP); Takao Takiguchi, Tokyo (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 937 days.

(21) Appl. No.: 11/771,249

(22) Filed: Jun. 29, 2007

(65) Prior Publication Data

US 2008/0007161 A1 Jan. 10, 2008

(30) Foreign Application Priority Data

Jul. 5, 2006 (JP) ................................. 2006-185488

(51) Int. Cl.
*H01L 51/54* (2006.01)
*H01J 1/62* (2006.01)
*C07C 13/48* (2006.01)
*C07C 211/54* (2006.01)
*C07D 213/06* (2006.01)

(52) U.S. Cl. ........ 428/690; 428/917; 313/504; 546/255; 564/427; 585/26

(58) Field of Classification Search .................. None
See application file for complete search history.

(56) References Cited

U.S. PATENT DOCUMENTS

| 3,391,068 | A | * | 7/1968 | Rauhut | 313/358 |
| 3,399,137 | A | * | 8/1968 | Bollyky et al. | 252/700 |
| 5,989,737 | A | * | 11/1999 | Xie et al. | 428/690 |
| 6,824,894 | B2 | | 11/2004 | Takiguchi et al. | 428/690 |
| 7,238,435 | B2 | | 7/2007 | Kamatani et al. | 428/690 |
| 7,387,845 | B2 | * | 6/2008 | Saitoh et al. | 428/690 |
| 2004/0067387 | A1 | * | 4/2004 | Kim et al. | 428/690 |
| 2005/0238913 | A1 | * | 10/2005 | Kelly et al. | 428/690 |
| 2006/0003171 | A1 | | 1/2006 | Igawa et al. | 428/447 |
| 2006/0066225 | A1 | | 3/2006 | Kishino et al. | 313/504 |
| 2007/0231600 | A1 | * | 10/2007 | Kamatani et al. | 428/690 |
| 2007/0232803 | A1 | * | 10/2007 | Kamatani et al. | 546/2 |

FOREIGN PATENT DOCUMENTS

JP 2004-342391 * 12/2004

OTHER PUBLICATIONS

Machine generated translation for JP 2004-342391 A, which was published Dec. 2004.*
Baldo et al., "Very High-efficiency Green Organic Light-emitting Devices Based on Electrophosphorescence," *App. Phys. Lett.*, vol. 75, No. 1, 4-6 (1999).
Burroughes et al., "Light-emitting Diodes Based on Conjugated Polymers," *Nature*, vol. 347, 539-541 (1990).
Chen et al., "Recent Developments in Molecular Organic Electroluminescent Materials," *Macromol. Symp.*, vol. 125, 1-48 (1997).
Van Gorkom et al., "Micromagnetics and Magnetoresistance of a Permalloy Point Contact," *Appl. Phys. Lett.*, vol. 74, No. 3, 422-424, (1999).

* cited by examiner

*Primary Examiner* — Dawn L Garrett
(74) *Attorney, Agent, or Firm* — Fitzpatrick, Cella, Harper & Scinto

(57) ABSTRACT

A novel compound for an organic EL device is provided which has a structure represented by the general formula (1):

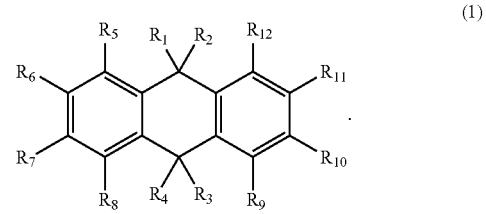

10 Claims, 3 Drawing Sheets

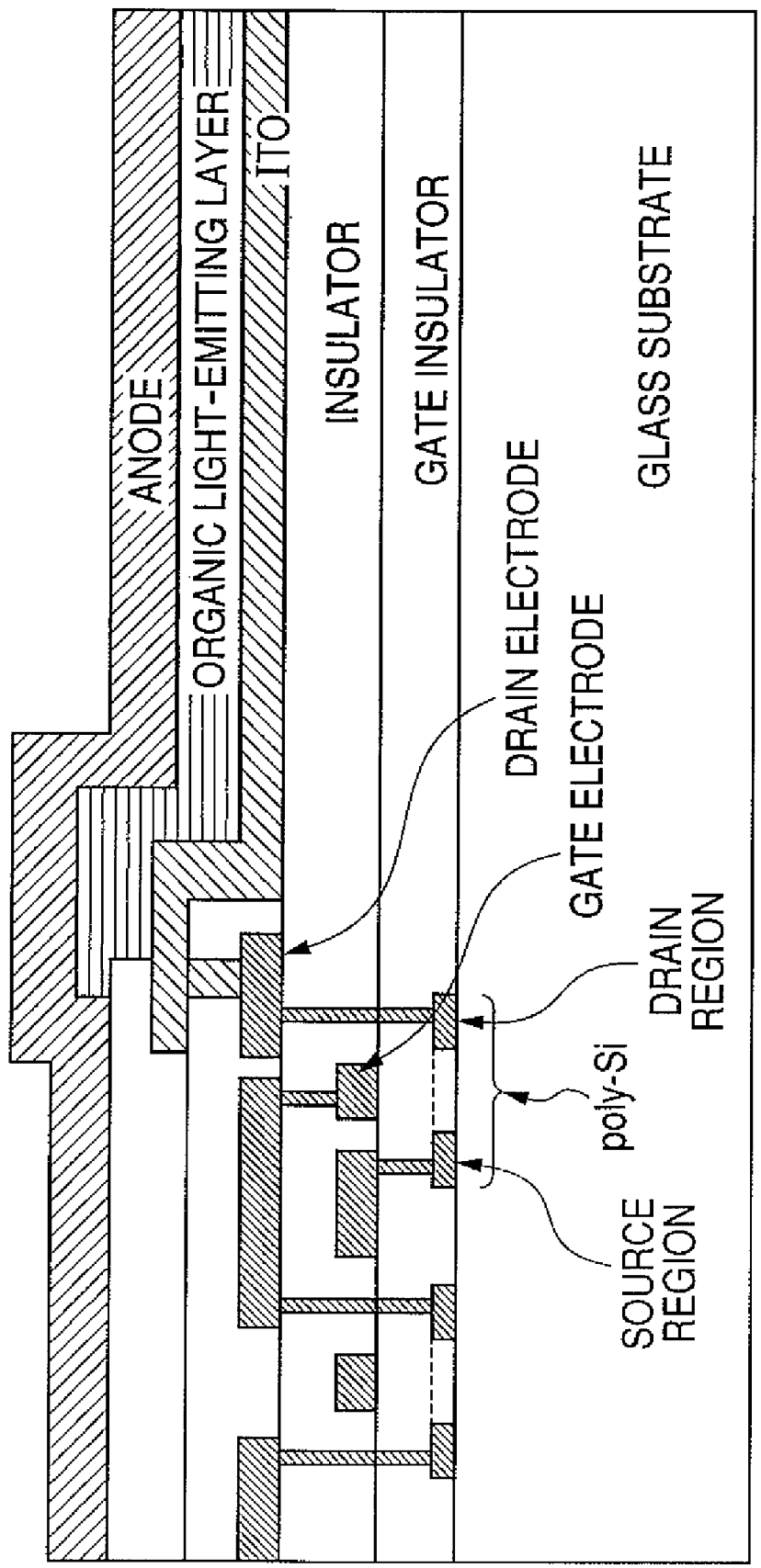

COMPOUND FOR ORGANIC EL DEVICE AND LIGHT-EMITTING DEVICE

BACKGROUND OF THE INVENTION

1. Field of the Invention

The present invention relates to a novel organic compound for an organic EL device (organic electroluminescence device) and an organic light-emitting device for use in, for example, a surface light source or a flat panel display.

2. Description of the Related Art

As detailed in Macromol. Symp. 125, 1-48 (1997), an organic EL device is generally structured to have two (upper and lower) electrodes formed on a transparent substrate and an organic substance layer including a light-emitting layer formed between the electrodes.

Recently, investigation has been made into a device using not only conventional light emission utilizing fluorescence upon transition from singlet exciton to ground state but also phosphorescence via triplet exciton as typified by D. F. O'Brien et al, "Improved energy transfer in electrophosphorescent device", Applied Physics Letters, Vol. 74, No. 3, p. 422 (1999) and M. A. Baldo et al, "Very high-efficiency green organic light-emitting devices based on electrophosphorescence", Applied Physics Letters, Vol. 75, No. 1, p. 4 (1999). In these articles, an organic layer having a four-layer structure is mainly used.

In addition to the organic light-emitting devices using such low-molecular materials as those described above, a group of the University of Cambridge has reported organic light-emitting devices using conjugate polymers (Nature, 347, 539 (1990)). This report has confirmed that light emission can be obtained by a single layer by forming polyphenylene vinylene (PPV) in a film shape by use of a coating system.

Recent progress of an organic light-emitting device is remarkable, and is characterized in that a highly responsive, thin, and lightweight light-emitting device that can be driven at a low applied voltage and provides a high luminance and a variety of emission wavelengths can be made, which suggests the applicability to a wide variety of uses.

However, at present, an optical output of a higher luminance and a higher conversion efficiency have been required. In addition, there still remain a large number of problems in terms of durability such as a change over time during long-term use and degradation due to an atmospheric gas containing oxygen or to moisture. Furthermore, light emission of blue, green and red colors having a high color purity is necessary when application to a full-color display or the like is attempted. However, those problems have not been sufficiently solved yet.

In addition, a large number of aromatic compounds and condensed polycyclic aromatic compounds have been studied as fluorescent organic compounds used for an electron-transporting layer, a light-emitting layer, and the like. However, it is difficult to say that a compound sufficiently satisfying the emission luminance and durability requirements has been already obtained. Further, there is no disclosure of the below-mentioned organic compound of the present invention containing a tetrahydroanthracene skeleton in which substituents at positions 9 and 10 are not joined to form a ring.

SUMMARY OF THE INVENTION

The present invention provides a novel compound for an organic EL device and an organic EL device using the compound, having an optical output with high efficiency and high luminance. The present invention also provides an organic EL device having high durability. Further, the present invention provides an organic EL device that can easily be produced at a relatively low cost.

According to an aspect of the present invention, there is provided a compound for an organic EL device having a structure represented by the following general formula (1):

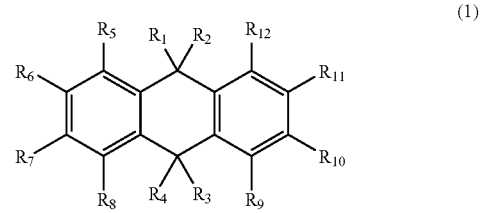

(1)

wherein $R_1$, $R_2$, $R_3$, and $R_4$ each represent, independently of one another, a halogen atom, a linear or branched alkyl group having 1 to 20 carbon atoms in which one methylene group or at least two non-adjacent methylene groups of the alkyl group may be replaced by —O—, —S—, —CO—, —CO—O—, —O—CO—, —CH=CH—, or —C≡C—, at least one methylene group of the alkyl group may be replaced by an arylene group which may have a substituent or by a divalent heterocyclic group which may have a substituent, and hydrogen atom(s) of the alkyl group may be substituted with fluorine atom(s)), an amino group which may have a substituent, a silyl group which may have a substituent, an aryl group which may have a substituent, or a heterocyclic group which may have a substituent; and $R_5$, $R_6$, $R_7$, $R_8$, $R_9$, $R_{10}$, $R_{11}$, and $R_{12}$ each represent, independently of one another, a hydrogen atom, a halogen atom, a linear or branched alkyl group having 1 to 20 carbon atoms in which one methylene group or at least two non-adjacent methylene groups of the alkyl group may be replaced by —O—, —S—, —CO—, —CO—O—, —O—CO—, —CH=CH—, or —C≡C—, at least one methylene group of the alkyl group may be replaced by an arylene group which may have a substituent or by a divalent heterocyclic group which may have a substituent, and hydrogen atom(s) of the alkyl group may be substituted with fluorine atom(s)), an amino group which may have a substituent, a silyl group which may have a substituent, a phenyl, naphthyl, pyrenyl, fluorenyl, phenanthrenyl, chrysenyl, fluoranthenyl, triphenylenyl, or tetraphenylanthracenyl group which may have a substituent, or a heterocyclic group which may have a substituent, and adjacent ones of $R_5$, $R_6$, $R_7$, $R_8$, $R_9$, $R_{10}$, $R_{11}$, and $R_{12}$ may be joined to form a ring structure.

Further, according to another aspect of the present invention, there is provided a compound for an organic EL device having a structure represented by the following general formula (2):

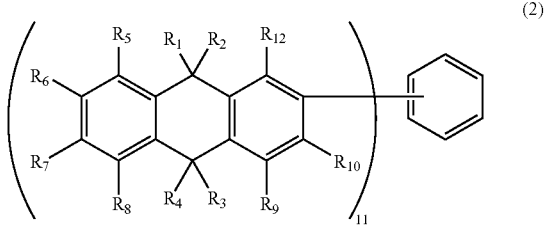

(2)

wherein $R_1$, $R_2$, $R_3$, and $R_4$ each represent, independently of one another, a halogen atom, a linear or branched alkyl group having 1 to 20 carbon atoms in which one methylene group or at least two non-adjacent methylene groups of the alkyl group may be replaced by —O—, —S—, —CO—, —CO—O—, —O—CO—, —CH=CH—, or —C≡C—, at least one methylene group of the alkyl group may be replaced by an arylene group which may have a substituent or by a divalent heterocyclic group which may have a substituent, and hydrogen atom(s) of the alkyl group may be substituted with fluorine atom(s)), an amino group which may have a substituent, a silyl group which may have a substituent, an aryl group which may have a substituent, or a heterocyclic group which may have a substituent;

$R_5$, $R_6$, $R_7$, $R_8$, $R_9$, $R_{10}$, and $R_{12}$ each represent, independently of one another, a hydrogen atom, a halogen atom, a linear or branched alkyl group having 1 to 20 carbon atoms in which one methylene group or at least two non-adjacent methylene groups of the alkyl group may be replaced by —O—, —S—, —CO—, —CO—O—, —O—CO—, —CH=CH—, or —C≡C—, at least one methylene group of the alkyl group may be replaced by an arylene group which may have a substituent or by a divalent heterocyclic group which may have a substituent, and hydrogen atom(s) of the alkyl group may be substituted with fluorine atom(s)), an amino group which may have a substituent, a silyl group which may have a substituent, a phenyl, naphthyl, pyrenyl, fluorenyl, phenanthrenyl, chrysenyl, fluoranthenyl, triphenylenyl, tetraphenylanthracenyl group which may have a substituent, or a heterocyclic group which may have a substituent, and adjacent ones of $R_5$, $R_6$, $R_7$, $R_8$, $R_9$, $R_{10}$, $R_{11}$, and $R_{12}$ may be joined to form a ring structure;

n represents an integer of 2 to 6; and hydrogen atom(s) of the central benzene ring may be replaced by nitrogen atom(s).

The organic EL device using the novel compound of the present invention, especially for a light-emitting material or host material of a light-emitting layer, has an optical output with high efficiency and high luminance, has high durability, and can easily be produced at a relatively low cost.

Further features of the present invention will become apparent from the following description of exemplary embodiments with reference to the attached drawings.

BRIEF DESCRIPTION OF THE DRAWINGS

FIG. 4 is a schematic view illustrating an example of a sectional structure of a TFT substrate.

DESCRIPTION OF THE EMBODIMENTS

Figure 1A:
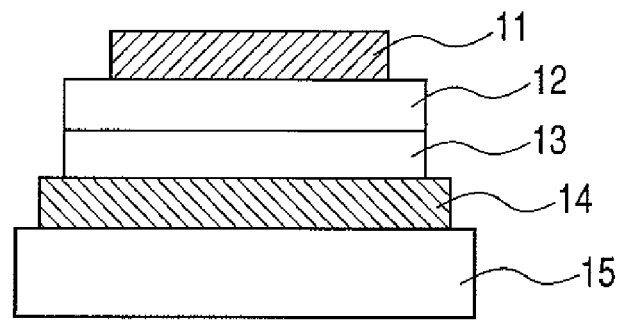
FIGS. 1A, 1B and 1C are views each illustrating an example of an organic EL device of the present invention.

First, the compound for an organic EL device of the present invention will be described.

The compound for an organic EL device of the present invention is characterized by having, in the molecule, a tetrahydroanthracene skeleton having substituents at positions 9 and 10.

In the compound for an organic EL device of the present invention, by forming sp3 bonds at positions 9 and 10 of anthracene to disrupt conjugation of the central portion, a higher bandgap and a higher T1 (lowest triplet excited state) with respect to the molecular weight can be attained. This is considered to be the reason for the attainment of charge transportability without quenching in luminescence in a light-emitting material and increase of emission efficiency and improvement in durability. Therefore, the compound for an organic EL device of the present invention is especially effective as a light-emitting material with a high T1, a host material for a phosphorescent material or fluorescent material having a maximum emission wavelength of 500 nm or less, a charge transporting material, or a charge blocking material.

In the compound for an organic EL device of the present invention, since the positions 9 and 10 correspond to benzyl positions, $R_1$, $R_2$, $R_3$, and $R_4$ each represent a substituent other than a hydrogen atom. Further, in order to prevent lowering of the glass transition temperature, it is desirable that $R_1$, $R_2$, $R_3$, and $R_4$ are each not a flexible cyclic group consisting entirely of sp3 carbons such as a cyclohexyl group but are each a long chain alkyl such as methyl group or ethyl group or an aromatic ring group. The compound for an organic EL device of the present invention is expected to have amorphous properties. In this point, $R_1$, $R_2$, $R_3$, and $R_4$ play an important role. $R_1$, $R_2$, $R_3$, and $R_4$ are preferably dimethyl groups and the like from the viewpoint of electroconductivity and glass transition temperature but are preferably dimethyl groups or those substituents having a longer chain length than dimethyl group from the viewpoint of solubility.

Further, there is no specific limitation to selection of $R_5$, $R_6$, $R_7$, $R_8$, $R_9$, $R_{10}$, $R_{11}$, and $R_{12}$, and substituents can be introduced in accordance with electroconductivity or bandgap, glass transition temperature and T1 level of molecules. For example, there can be introduced an alkyl group, aromatic ring group, heterocyclic group, silyl group, or ether group which may have a constituent and a constituent containing a heteroatom with charge transportability.

The solubility, HOMO-LUMO, triplet level, and mobility of the compound for an organic EL device of the present invention can be adjusted by introduction of substituents into the tetrahydroanthracene skeleton, formation of repeating structure, increase in molecular mass, or mixing of two or more compounds. Therefore, the compound for an organic EL device of the present invention can be used for a hole injection material, an electron injection material, a hole-transporting material, an electron-transporting material, a light-emitting material, a host material for dispersion of a light-emitting material, an exciton diffusion prevention material, a charge injection material, and the like, depending on the species of substituents introduced or the kinds of other materials to be combined with. Further, the compound for an organic EL device of the present invention can be used to form an amorphous film by a vapor deposition, coating, inkjet, or lamination method.

The compound for an organic EL device of the present invention has a stable glassy state and can form a stable amorphous film by vapor deposition or the like. Moreover, the compound has a high solubility to organic solvents and can easily be purified by recrystallization or column chromatography.

Specific examples of the compound for an organic EL device of the present invention are shown below. However, these examples are merely representative examples, and the present invention is not limited thereto.

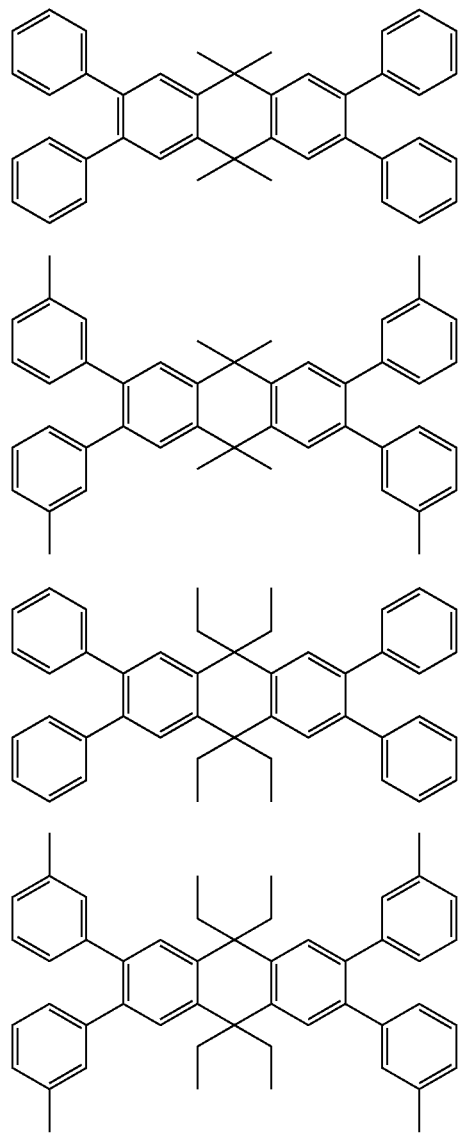
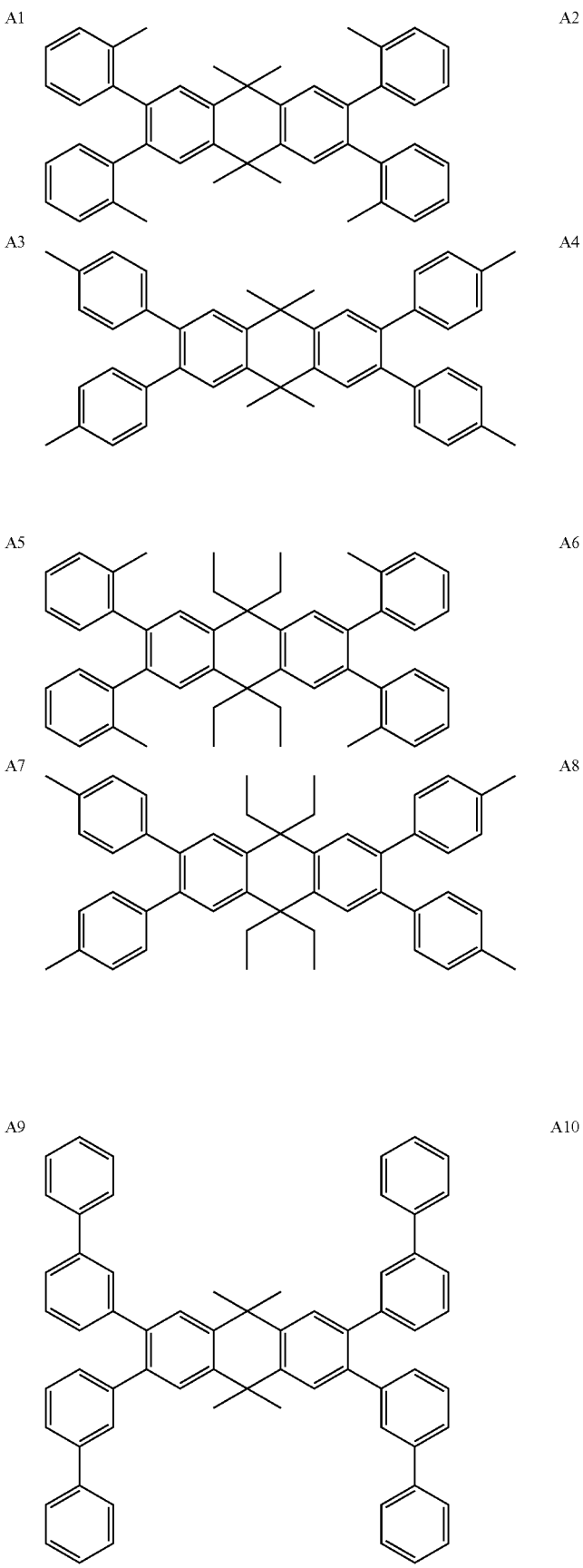

-continued
A11
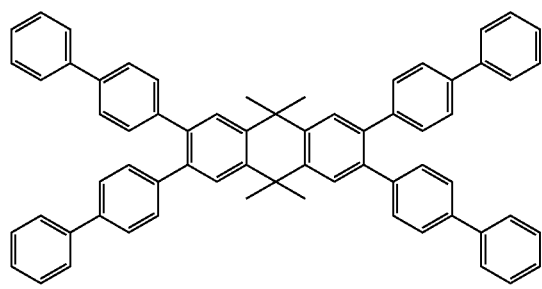
A12
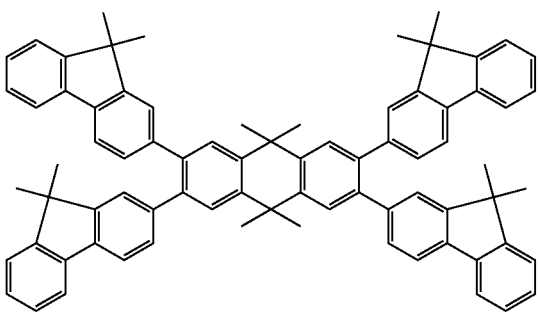
A13
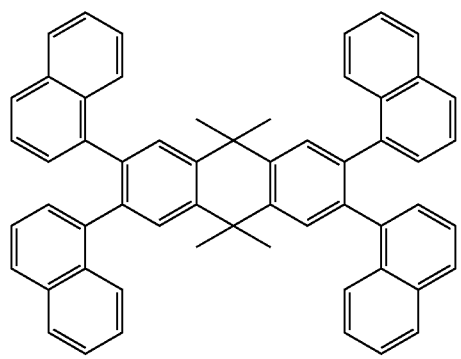
A14
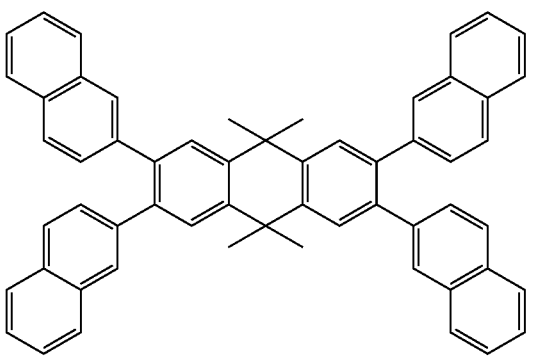
A15
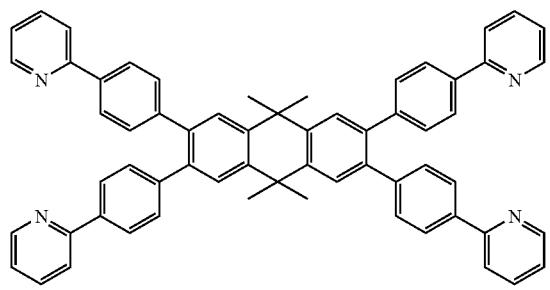
A16
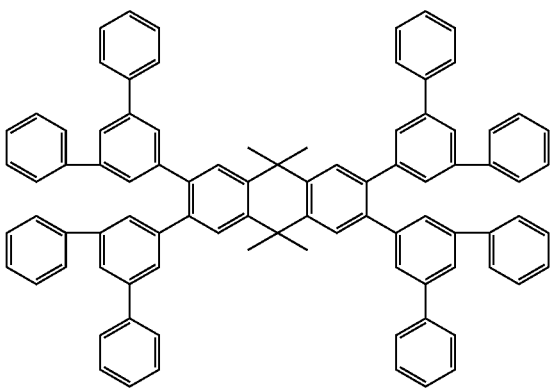
A17
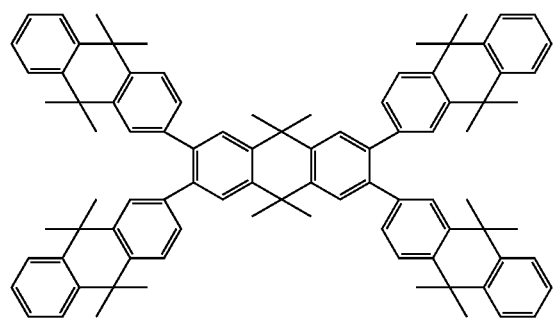
A18
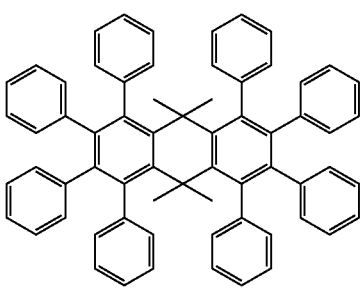

-continued
A19
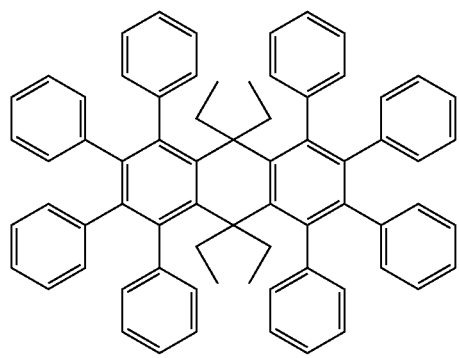
A20
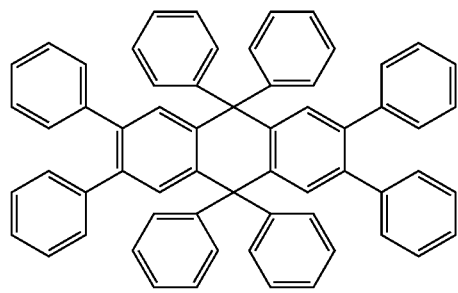
A21
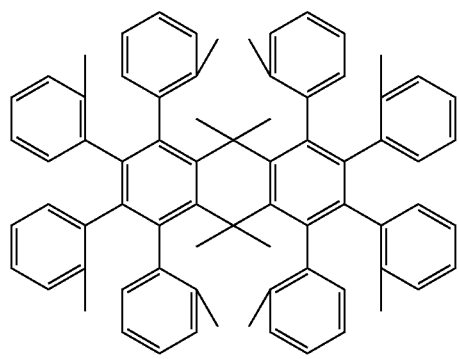
A22
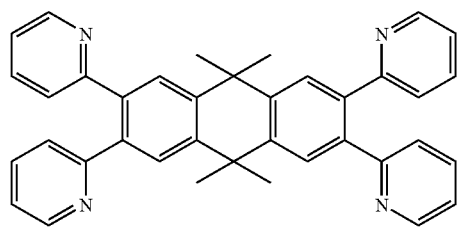
A23
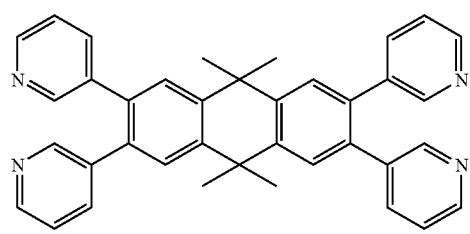
A24
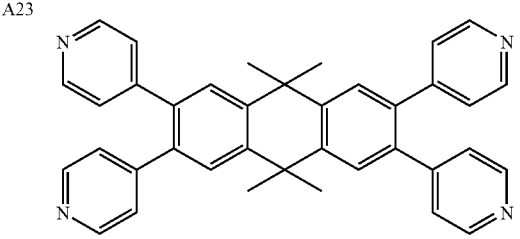
A25
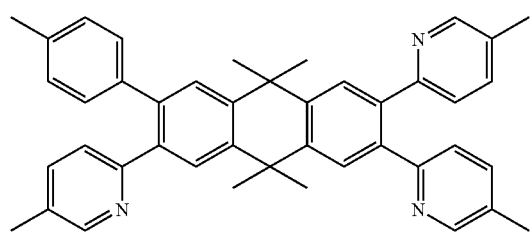
A26
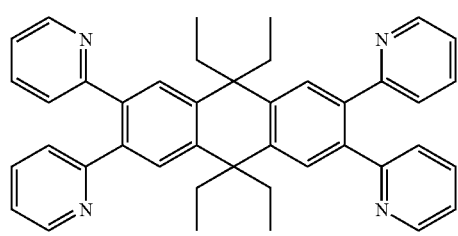
A27
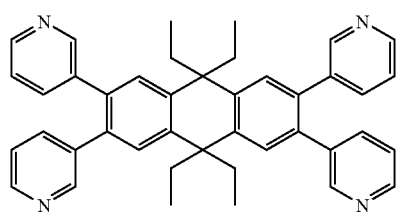
A28
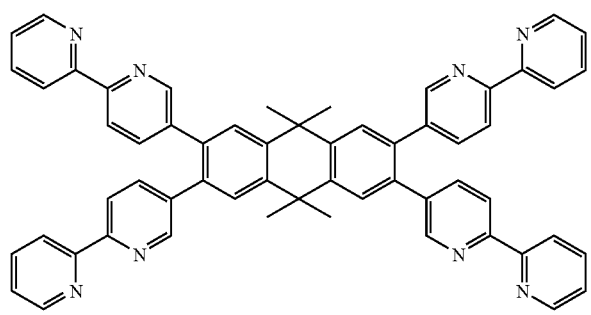

-continued
A29
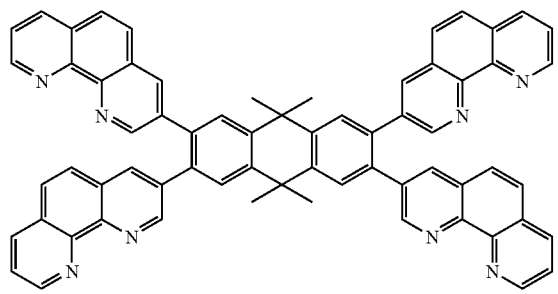
A30
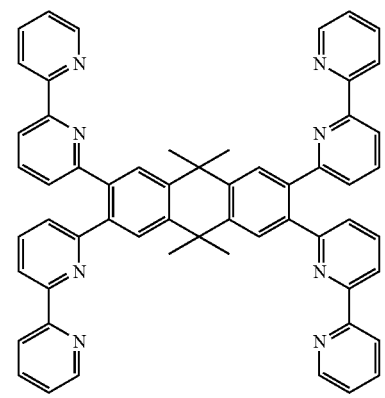
A31
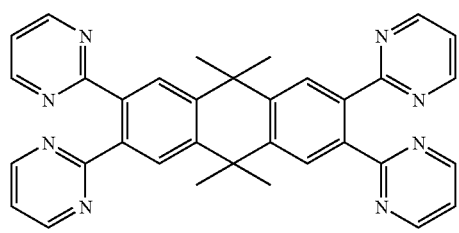
A32
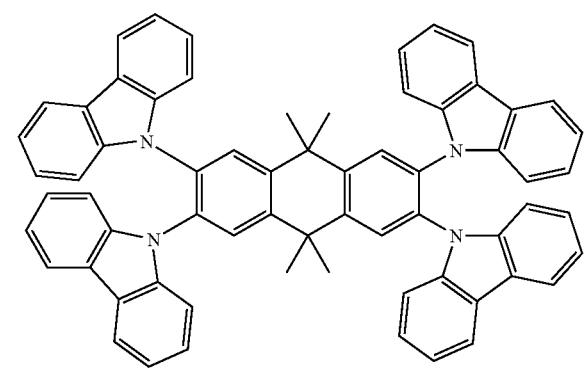
A33
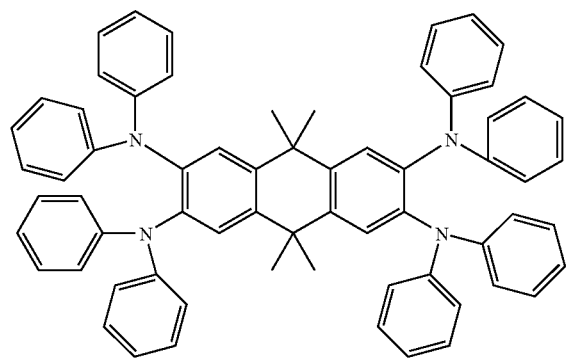
A34
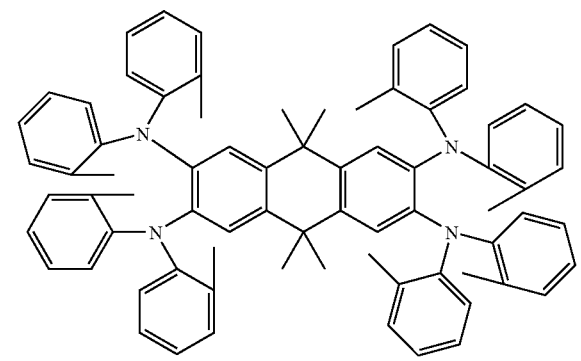
A35
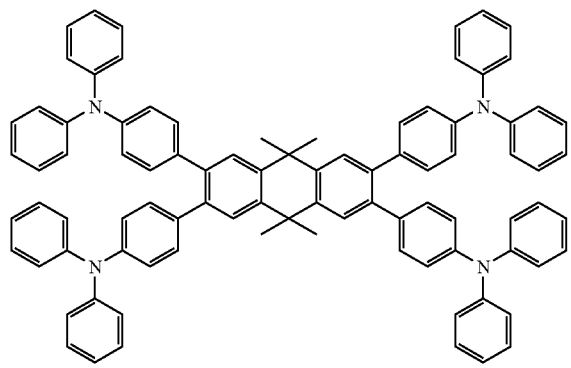
A36
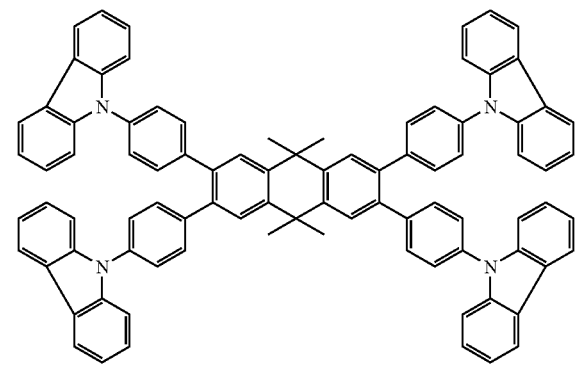

-continued
A37 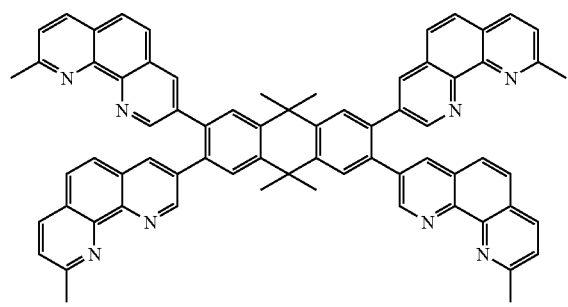
A38 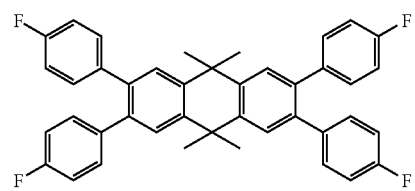
A39 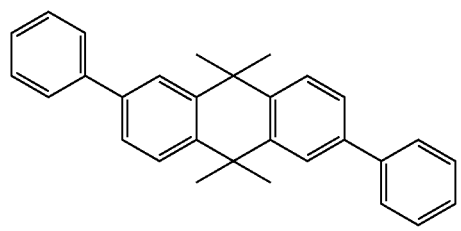
A40 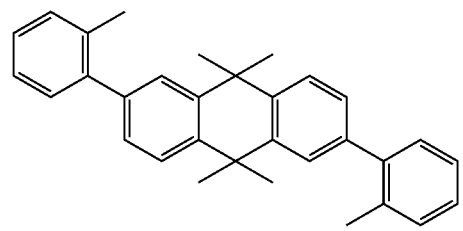
A41 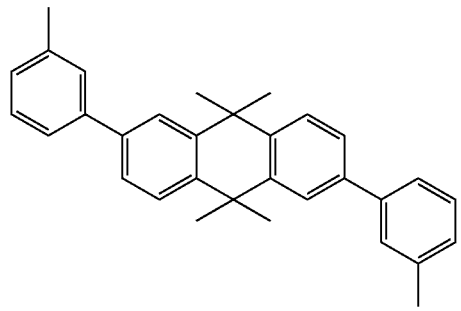
A42 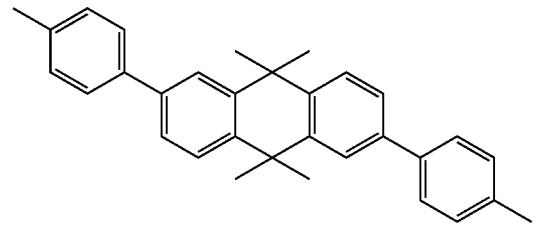
A43 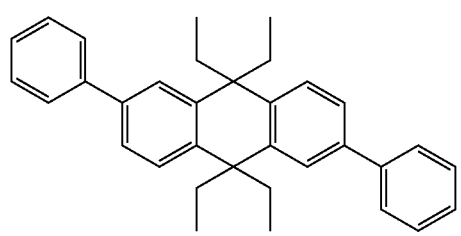
A44 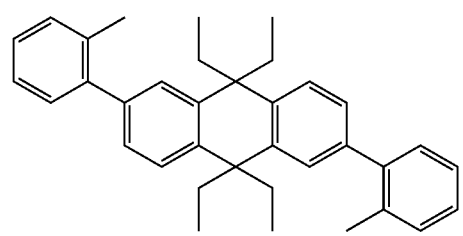
A45 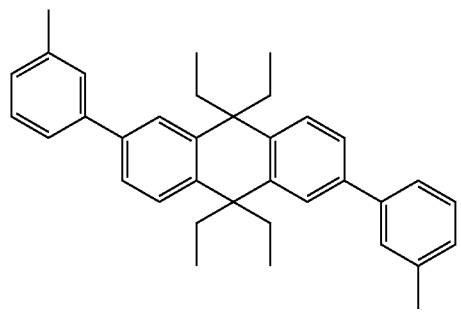
A46 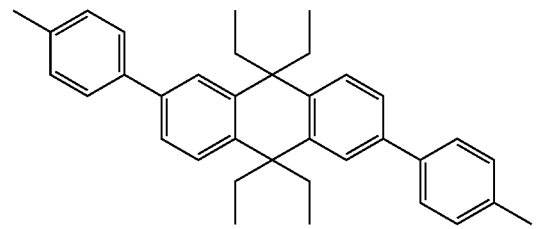

-continued
A47
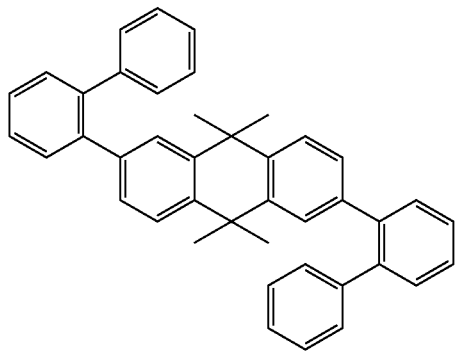
A48
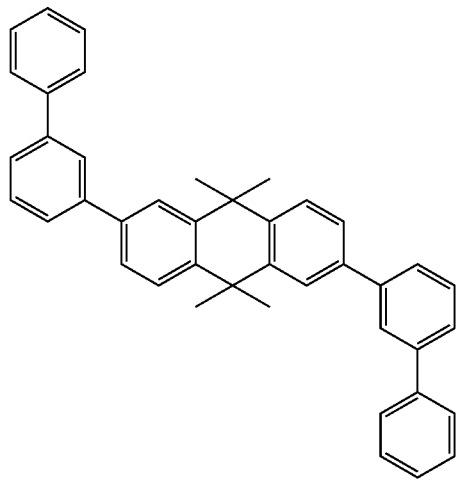
A49
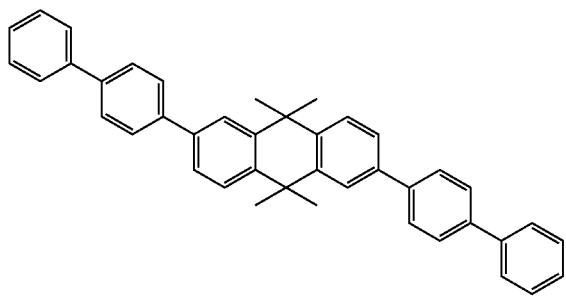
A50
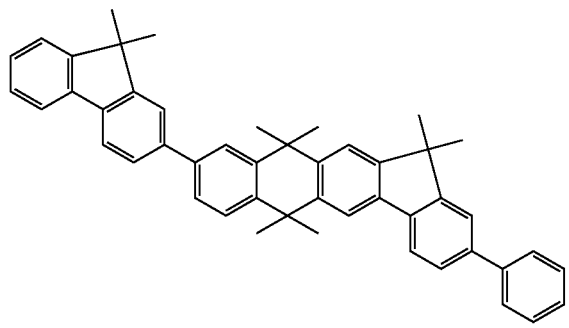
A51
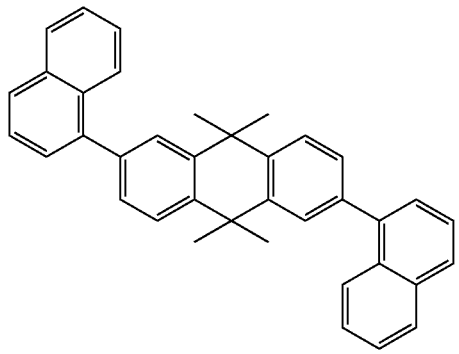
A52
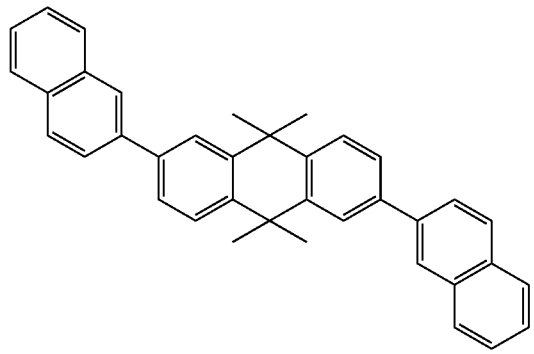
A53
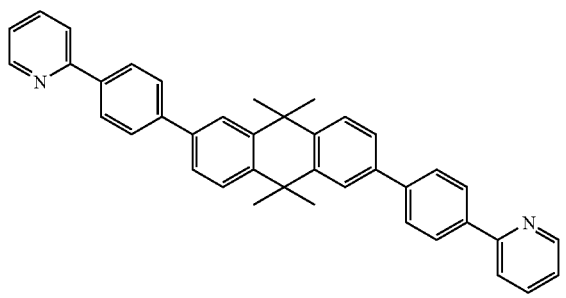
A54
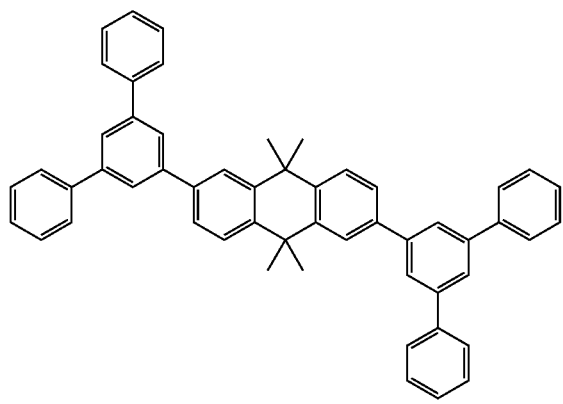

-continued
A55
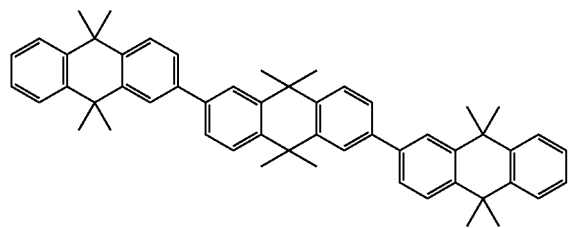
A56
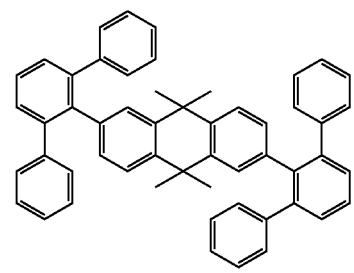
A57
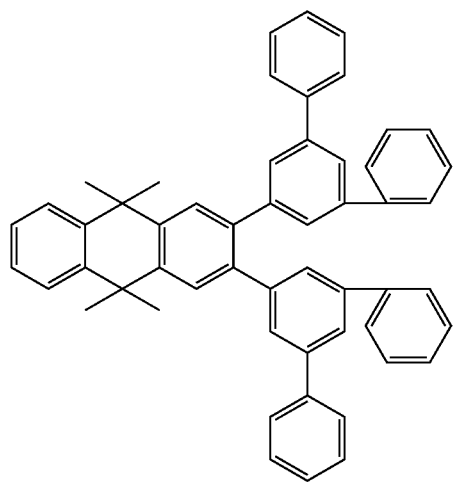
A58
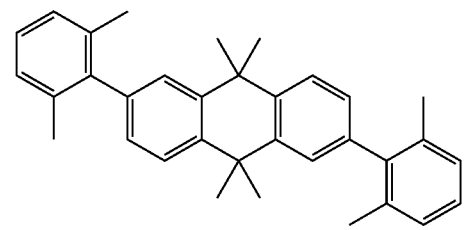
A59
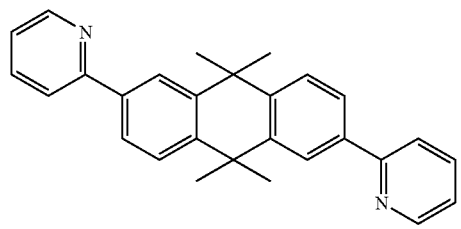
A60
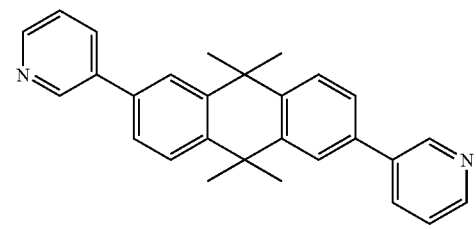
A61
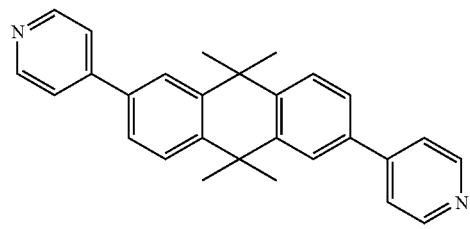
A62
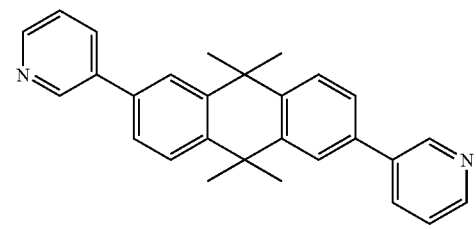
A63
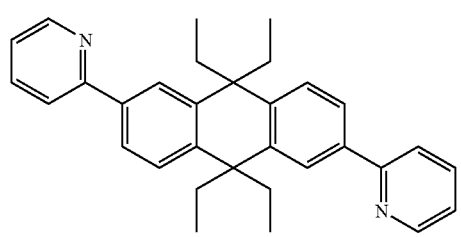
A64
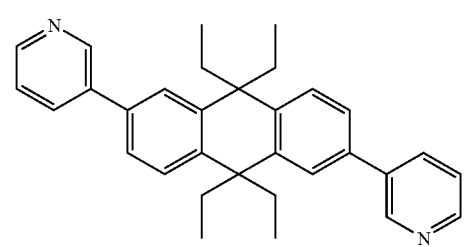

-continued
A65
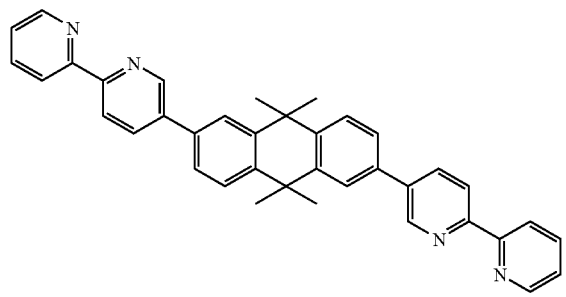
A66
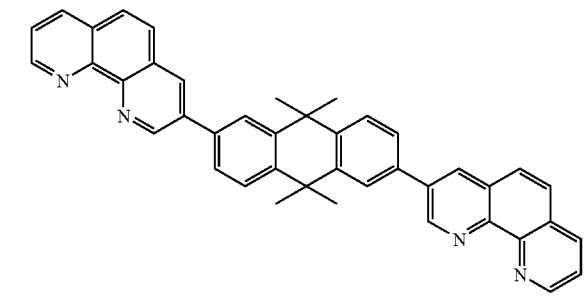
A67
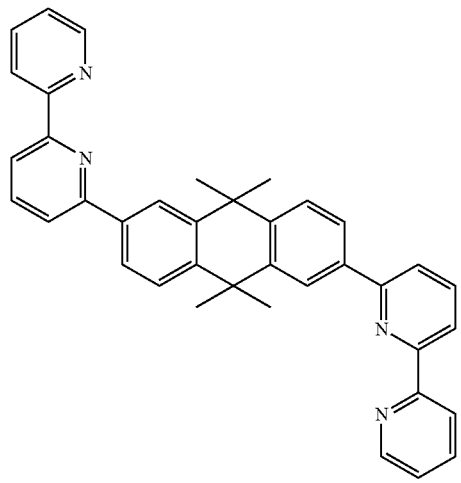
A68
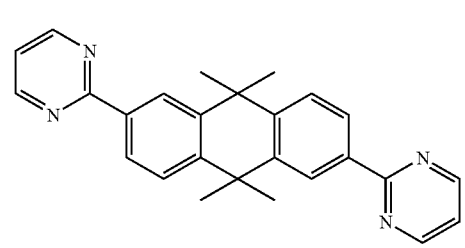
A69
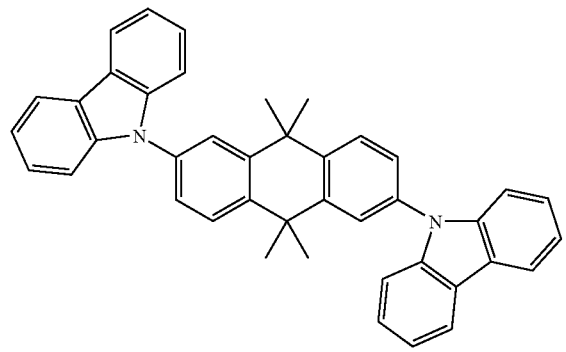
A70
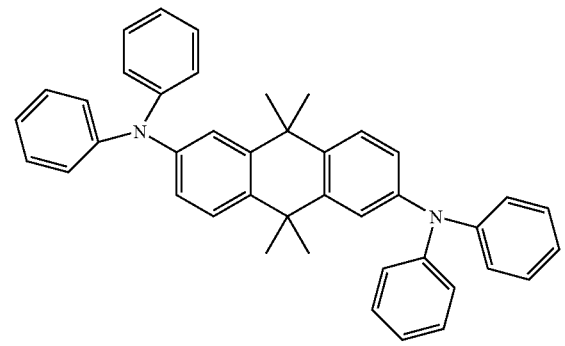
A71
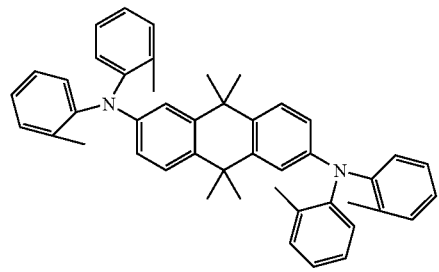
A72
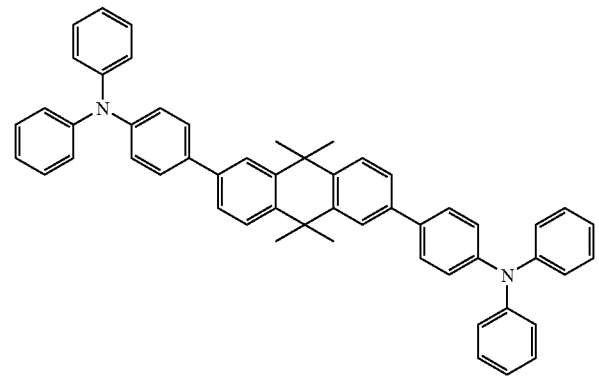

-continued
A73
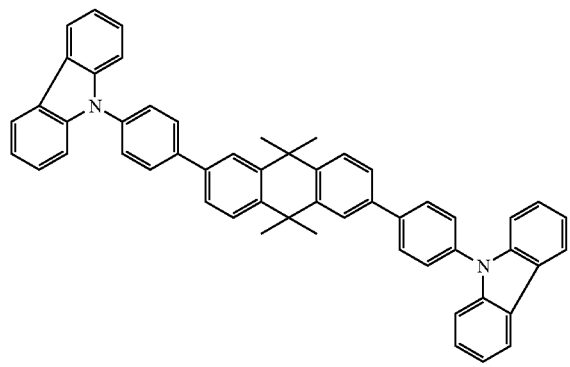
A74
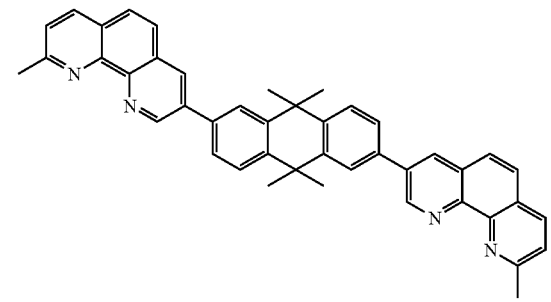
A75
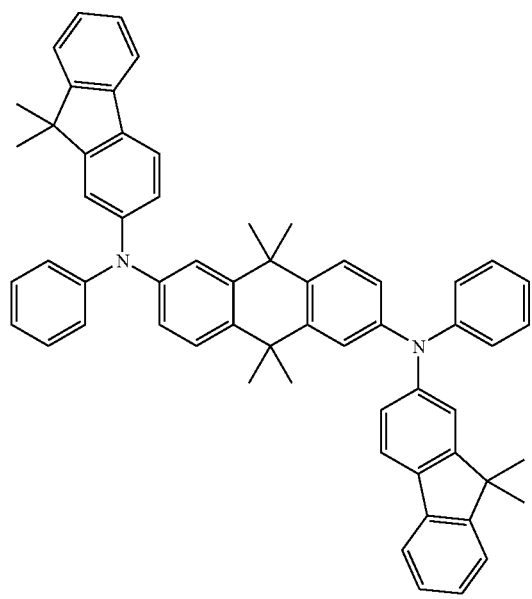
A76
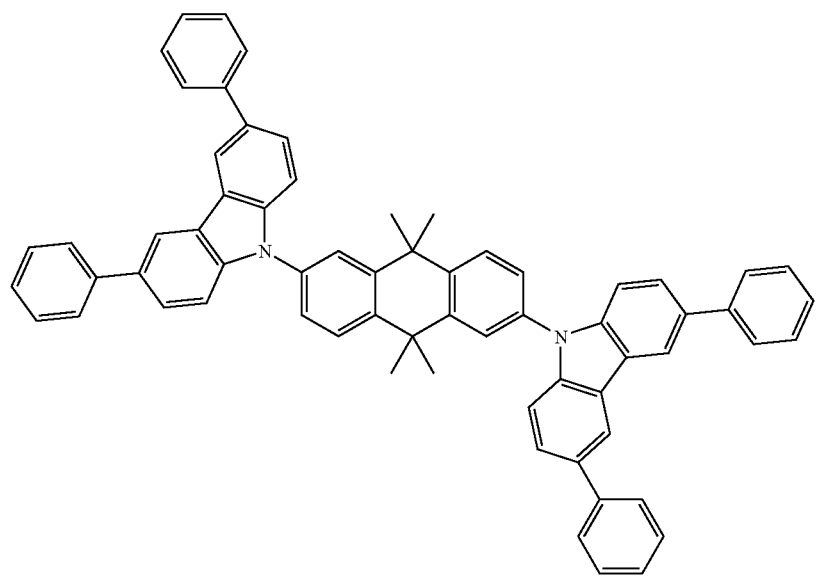

A77
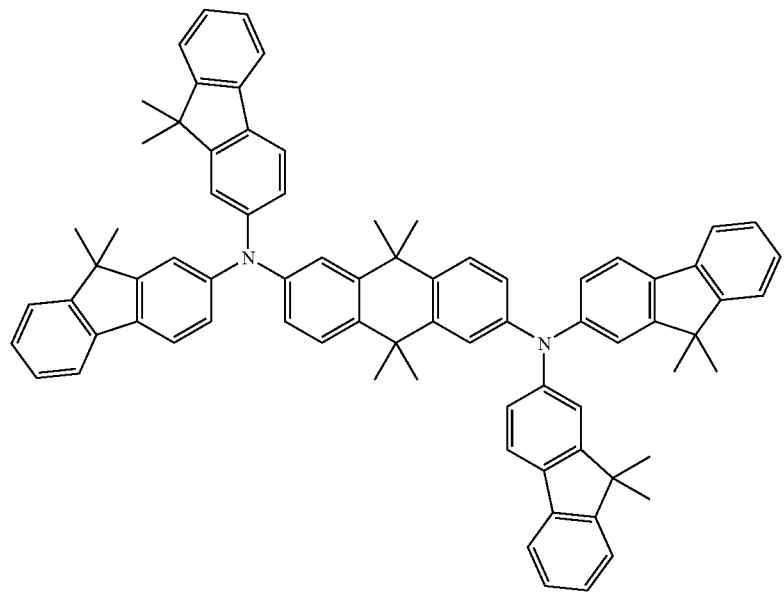
A78
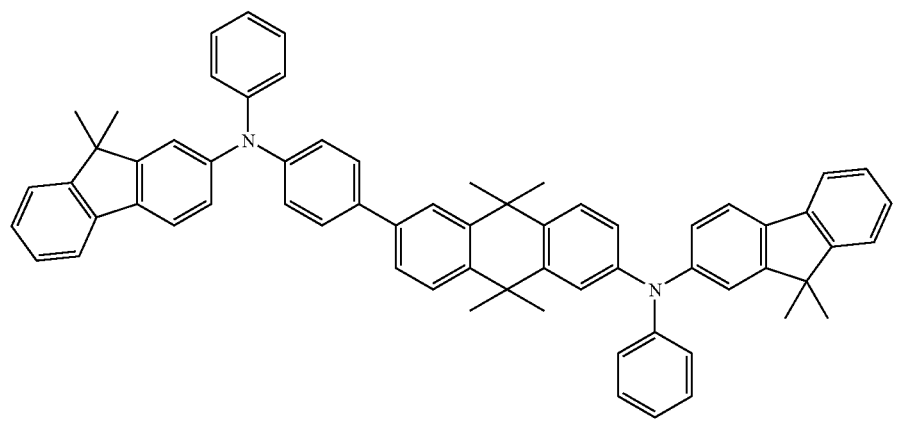
A79
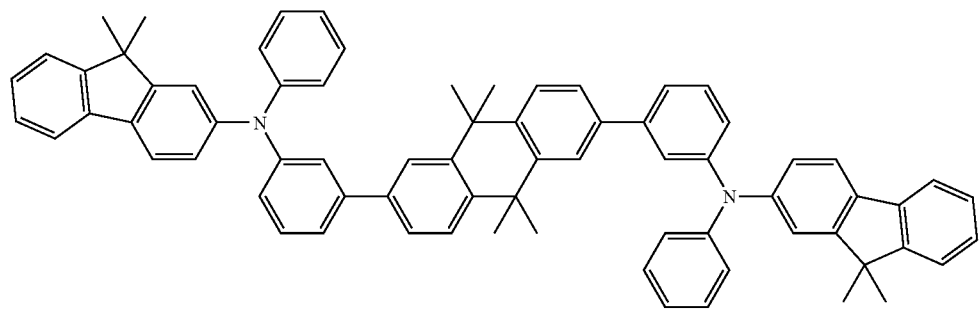

-continued
A83
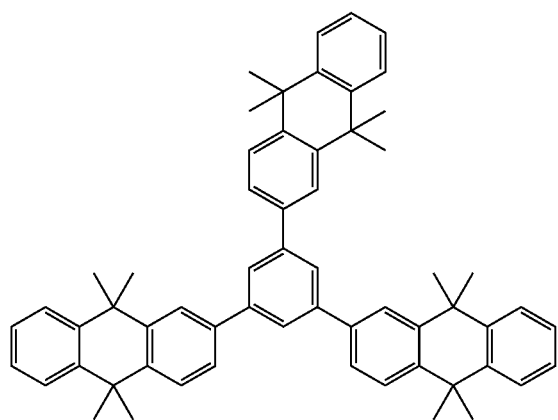
A84
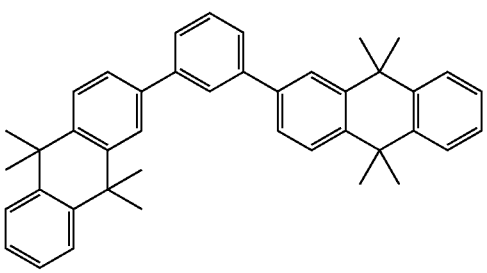
A85
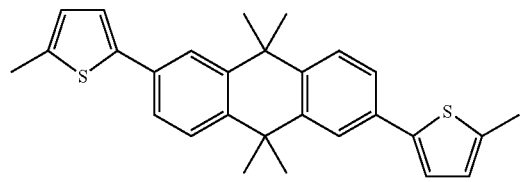
A86
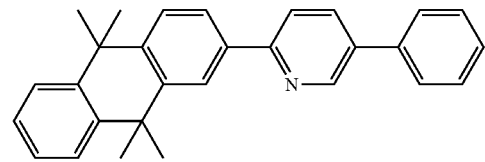
A87
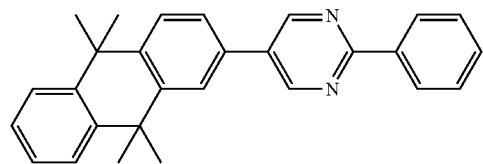
A88
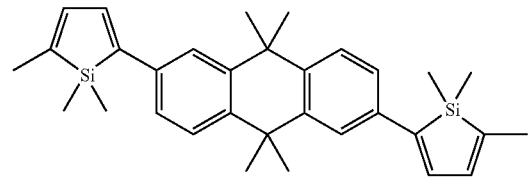
A89
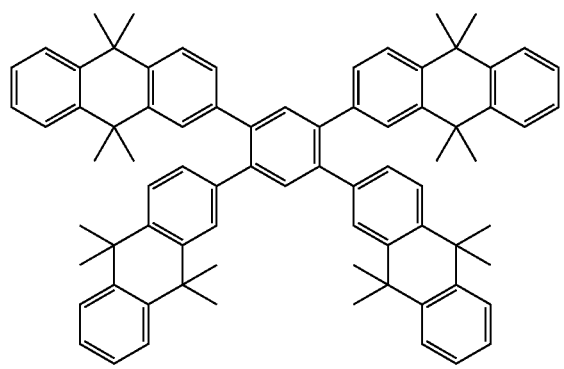
A90
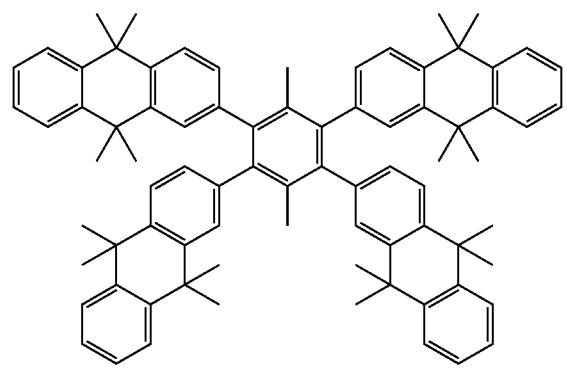

A91

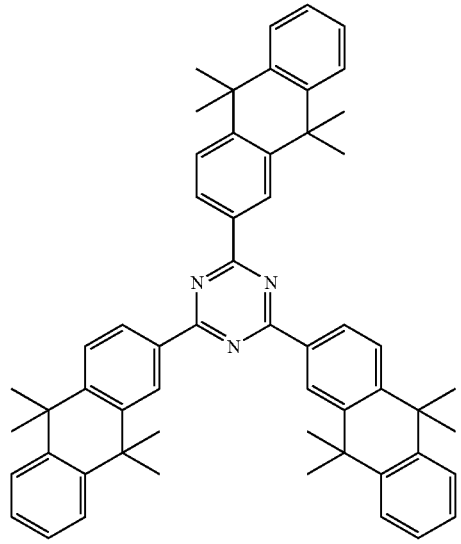

A92

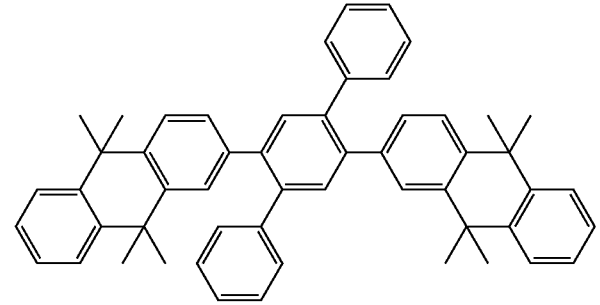

Next, the organic EL device of the present invention will be described.

Figure 1B:
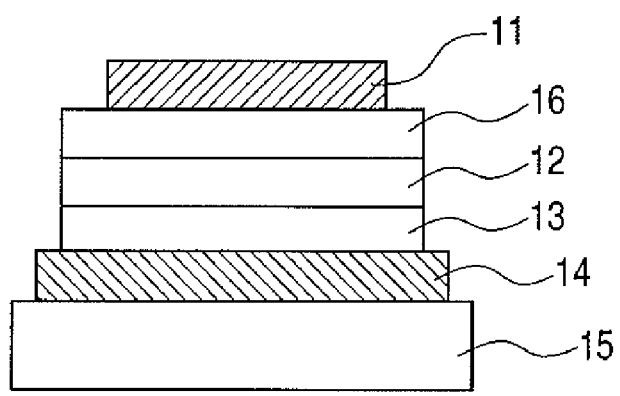
Figure 1C:
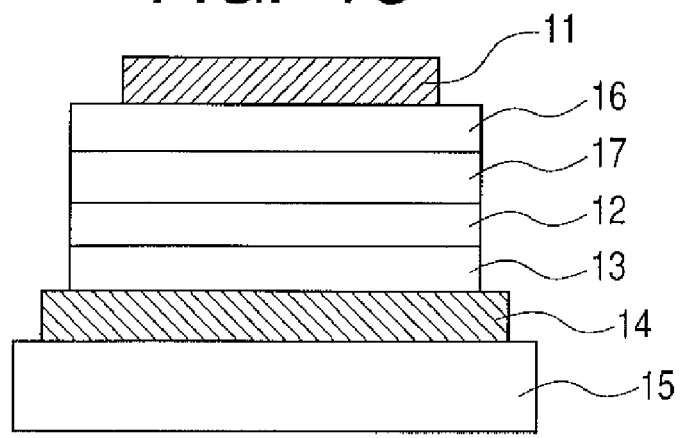

The organic EL device of the present invention has at least one organic compound layer. At least one of the at least one organic layer includes the above-described compound for an organic EL device of the present invention. Basic configurations of the organic EL device of the present invention are illustrated in FIGS. 1A, 1B and 1C. The organic EL device shown in each of FIGS. 1A, 1B and 1C is a device in which an organic compound layer is interposed between a pair of opposing electrodes, and a voltage is applied between the electrodes to emit light.

In the organic EL device shown in FIGS. 1A, 1B and 1C, on a transparent substrate 15, there are formed a transparent electrode 14 having a thickness of 50 nm or more and 200 nm or less, a plurality of organic compound layers, and a metal electrode 11 for interposing the plurality of organic compound layers between the transparent electrode 14 and the metal electrode 11.

FIG. 1A shows an example in which the organic compound layers include a light-emitting layer 12 and a hole-transporting layer 13. ITO having a large work function is used for the transparent electrode 14, so that holes can be easily injected from the transparent electrode 14 into the hole-transporting layer 13. A metal material having a small work function such as aluminum, magnesium, or an alloy using any one of them is used for the metal electrode 11, so that electrons can be easily injected to the organic compound layers.

For the light-emitting layer 12, the compound for an organic EL device of the present invention is preferably used, while for the hole-transporting layer 13, there can suitably be used an electron-donative material such as a triphenyldiamine (TPD) derivative typified by α-NPD.

The device having the structure as described above exhibits electrical rectifying property. When an electric field is applied such that the metal electrode 11 becomes a cathode and the transparent electrode 14 becomes an anode, electrons are injected from the metal electrode 11 into the light-emitting layer 12, while holes are injected from the transparent electrode 14 to the light-emitting layer 12.

The injected holes and electrons are recombined in the light-emitting layer 12 to generate excitons, thereby causing light emission. At this time, the hole-transporting layer 13 serves as an electron-blocking layer. As a result, the recombination efficiency at an interface between the light-emitting layer 12 and the hole-transporting layer 13 increases to thereby increase the emission efficiency.

Further, in FIG. 1B, an electron-transporting layer 16 is provided between the metal electrode 11 and the light-emitting layer 12 shown in FIG. 1A. The light-emitting function and electron/hole transporting functions are separated from each other to establish a more effective carrier blocking structure, whereby the emission efficiency is increased. For the electron-transporting layer 16, for example, an oxadiazole derivative can be used.

Further, as shown in FIG. 1C, a four-layer structure can preferably be adopted which includes the hole-transporting layer 13, the light-emitting layer 12, an exciton diffusion prevention layer 17, and the electron-transporting layer 16 in the stated order from the side of the transparent electrode 14 as the anode to the side of the metal electrode 11 as the cathode.

In the organic EL device of the present invention, it is desirable that the layer containing the compound for an organic EL device is a light-emitting layer, a hole-transporting layer, or an electron-transporting layer.

As the phosphorescent material, there can be used the generally known phosphorescent materials. In order to obtain an organic EL device with high efficiency, a metal coordinate compounds such as an Ir coordinate compound, a Pt coordinate compound, a Re coordinate compound, a Cu coordinate compound, a Eu coordinate compound, and a Rh coordinate compound are preferred, and the Ir coordinate compound, which is known to exhibit strong phosphorescence, is more preferred. Moreover, in order to allow a light-emitting layer to emit lights of a plurality of colors or to assist excitons or charge transmission, a plurality kinds of phosphorescent materials can be contained in a light-emitting layer.

The optical EL device having high efficiency according to the present invention can be applied to products which require energy saving or high luminance. Examples of such applications include a display apparatus, a light source of a printer, an illumination apparatus, and a backlight for a liquid crystal display apparatus. The application to the display apparatus can provide a lightweight and energy-saving flat panel display with a high level of visibility. In addition, for the light source of a printer, a laser light source of a laser beam printer which is widely used at present can be substituted by the organic EL device of the present invention. An image can be formed by disposing devices which can be addressed independently from one another on an array and by performing a desired exposure with respect to a photosensitive drum by use thereof. The use of the organic EL device of the present invention can significantly reduce the size of an apparatus. The organic EL device of the present invention is expected to provide an energy-saving effect on the illumination apparatus and the backlight.

The application to the display apparatus includes application to a display of a system in which the organic EL devices are driven using an active-matrix TFT drive circuit.

The image display apparatus of the present invention is characterized by including the organic EL device of the present invention and a unit for supplying an electrical signal to the organic EL device.

Hereinafter, an example in which an active matrix substrate is used in the device of the present invention will be described with reference to FIGS. 2, 3 and 4.

Figure 2:
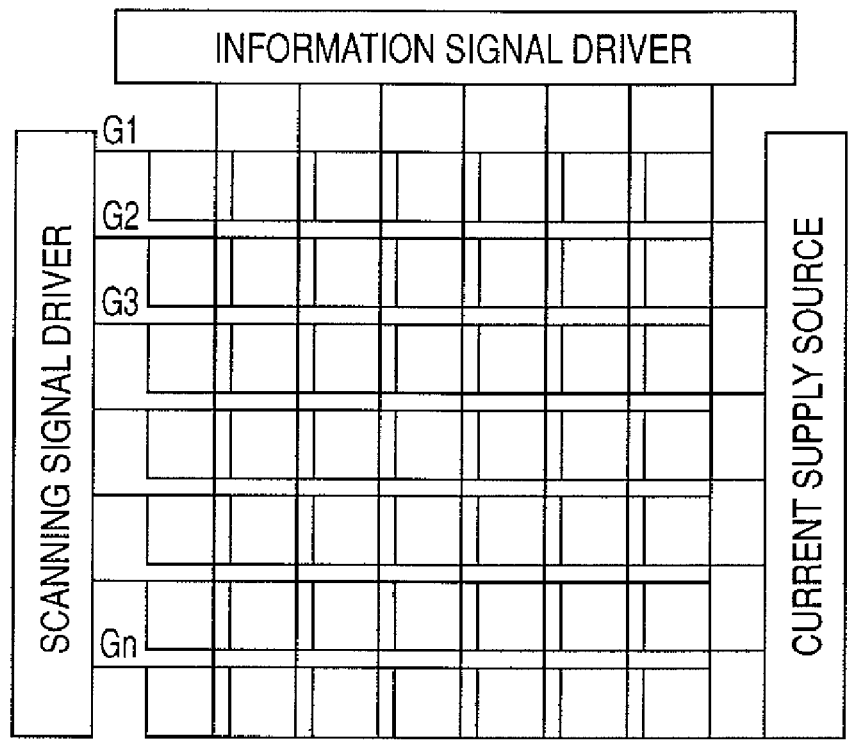
FIG. 2 is a diagram schematically illustrating an example of the constitution of a panel provided with an EL device and a driving unit.
Figure 3:
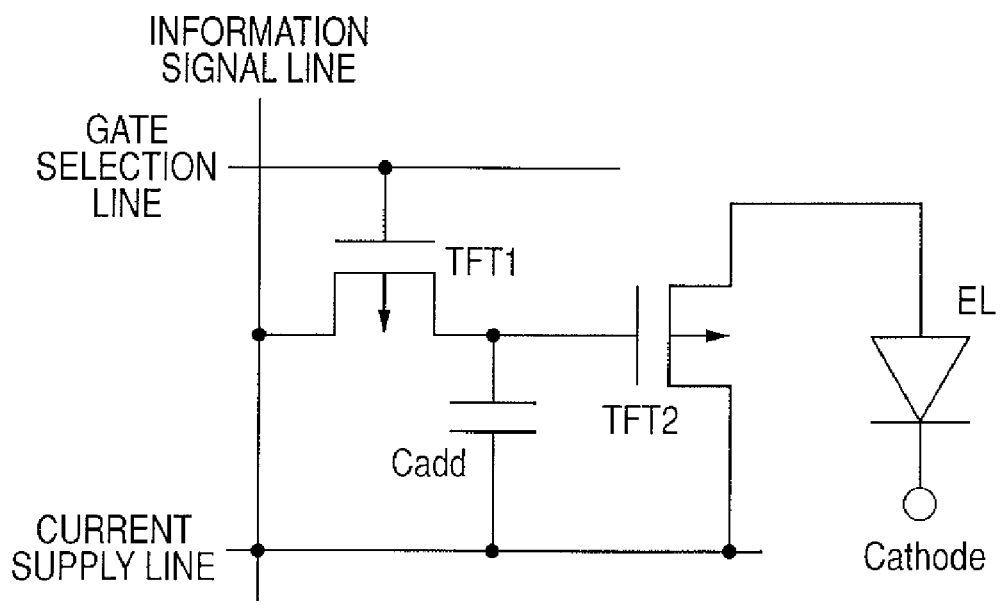
FIG. 3 is a diagram illustrating an example of a pixel circuit.

FIG. 2 schematically shows an example of the configuration of a panel provided with an EL device and a drive unit. A scanning signal driver, an information signal driver, and a current supply source are disposed on the panel, and are connected to gate selection lines, information signal lines, and current supply lines, respectively. A pixel circuit shown in FIG. 3 is disposed at the point of intersection of a gate selection line and an information signal line. The scanning signal driver selects gate selection lines G1, G2, G3, . . . , Gn sequentially, and an image signal is applied from the information signal driver in synchronization with the selection.

Next, the operation of the pixel circuit will be described. When a selection signal is applied to the gate selection line in the pixel circuit, a TFT 1 is turned on, an image signal is supplied to a Cadd, and the gate potential of a TFT 2 is determined. A current is supplied from the current supply line to the EL device in accordance with the gate potential of the TFT 2. Since the gate potential of the TFT 2 is kept in the Cadd until the TFT 1 is subjected to the subsequent scanning selection, the current continues to flow in the EL device by the subsequent scanning. As a result, the EL device can be caused to emit light at all times during one frame period.

FIG. 4 is a schematic view illustrating an example of a sectional structure of a TFT substrate to be used in the present invention. A p-Si layer is provided on a glass substrate, and each of channel, drain, and source regions is doped with a necessary impurity. A gate electrode is provided on the layer with a gate insulating film interposed between the electrode and the layer, and a drain electrode to be connected to the drain region and a source electrode to be connected to the source region are formed. An insulating layer and an ITO electrode as a pixel electrode are stacked on the electrodes, and the ITO electrode and the drain electrode are connected to each other through a contact hole.

The application of the present invention is not particularly limited to a switching device, and the present invention is easily applicable to, for example, a single crystal silicon substrate, a MIM device, or an a-Si type device.

An organic EL display panel can be obtained by sequentially stacking one or more organic EL layers and a cathode layer on the ITO electrode. An image with good image quality can be stably displayed for a long period of time by driving the display panel of the present invention.

EXAMPLES

Hereinafter, the present invention will be described specifically by way of examples. However, the present invention is not limited to those examples.

Example 1

Synthesis of Exemplified Compound A1

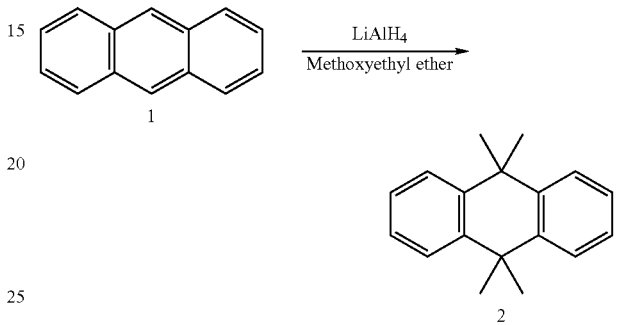

70.0 g (393 mmol) of anthracene (1), 37.4 g (986 mmol) of LiAlH$_4$, and 1100 mL of methoxyethylether were placed in a 2000 mL round bottom flask, and the mixture was stirred at 150° C. for 10 hours under nitrogen flow. The color of the reaction system changed from grey to blue, dark blue, and brown in the mentioned order. After the reaction solution was cooled, 6 L of 1N HCl was slowly added to the solution, LiAlH$_4$ was inactivated, extraction was performed with ethyl acetate (500 mL×4), and the organic layer was isolated and washed with distilled water three times. Then, concentration was performed, and the resulting solid matter is recrystallized with ethyl acetate/hexane to give 28.3 g of a crystal of 9,9,10,10-tetramethyl-9,10-dihydroanthracene (2) (30% yield).

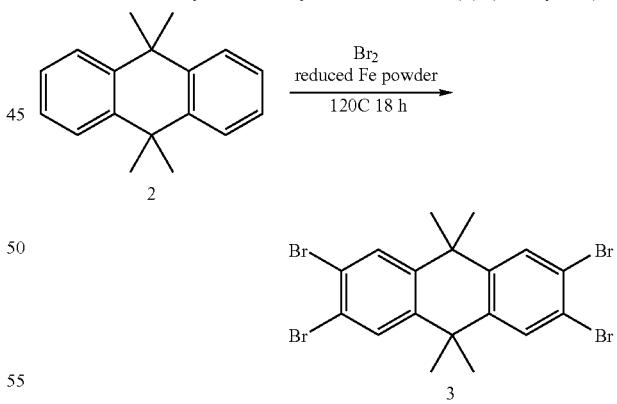

Under nitrogen flow, 5.0 g (21.2 mmol) of the compound (2), 40 mL of carbon tetrachloride, 13.6 g (84.8 mmol) of bromine, and 0.5 g (84.8 mmol) of reduced iron were placed in a 100 mL autoclave, and the mixture was heated to 120° C. and then stirred for 18 hours. After the completion of the reaction, the mixed liquid was cooled to room temperature, then the autoclave was opened while paying attention to the inner pressure, and the mixed liquid was added with 80 mL of chloroform and then filtered through celite. After the celite layer washed with chloroform (100 mL×3), the filtrate was concentrated. The residue was added with toluene and ultrasonically cleaned and a crystal was filtered off. The crystal was heated to reflux with toluene again to be dissolved, allowed to be cooled and recrystallized to give 5.6 g of a crystal rof a monotoluene adduct of the compound (3) (41% yield).

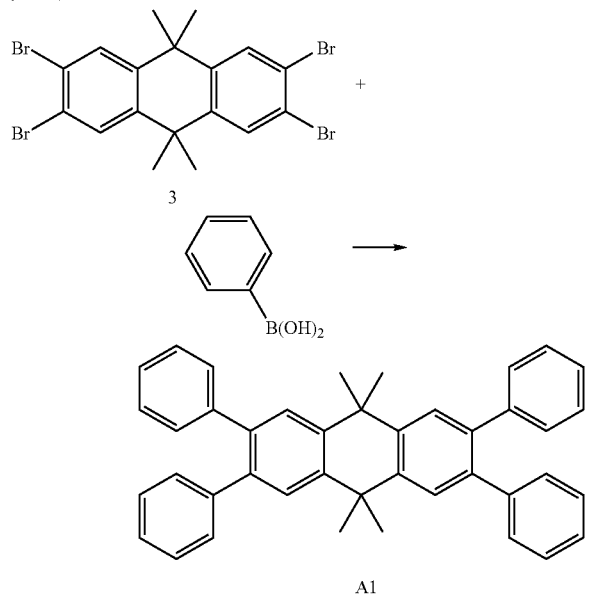

Under nitrogen flow, 1.1 g (2.0 mmol) of the compound (3), 1.21 g (10.0 mmol) of phenylboronic acid, 20 mL of toluene, 10 mL of ethanol, and 20 mL of 2M aqueous solution of sodium carbonate were placed in a 100 mL flask. After 150 mg of tetraxistriphenylphosphine palladium was input to the mixture, the mixture was stirred for 8 hours under heating and reflux. After the completion of the reaction, the reaction liquid was added with water, and the precipitate was filtered off. The precipitate was heated in chlorobenzene and dissolved, then the solution was allowed to be cooled to effect recrystallization, and sublimation purification was performed to give 0.6 g of a crystal of Exemplified Compound A1 (56% yield).

540.3 as M+ of the compound was confirmed by means of Matrix Assisted Laser Desorption/Ionization-Time of Flight Mass Spectrometry (MALDI-TOF MS).

The 5% decomposition temperature of the compound was 299° C.

Example 2

Synthesis of Exemplified Compound A10

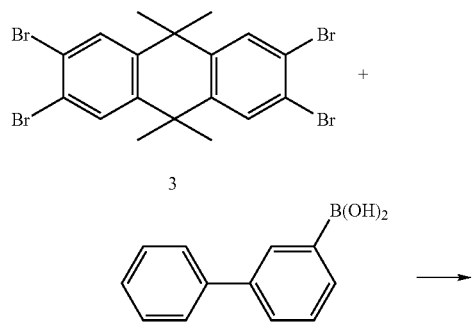

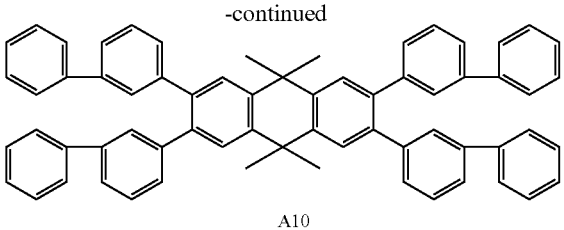

Under nitrogen flow, 1.1 g (2.0 mmol) of the compound (3), 1.98 g (10.0 mmol) of biphenylboronic acid, 20 mL of toluene, 10 mL of ethanol, and 20 mL of 2M aqueous solution of sodium carbonate were placed in a 100 mL flask. After 150 mg of tetraxistriphenylphosphine palladium was input to the mixture, the mixture was stirred for 8 hours under heating and reflux. After the completion of the reaction, the reaction liquid was added with water, and the precipitate was filtered off. The precipitate was heated in chlorobenzene and dissolved, then the solution was allowed to be cooled to effect recrystallization, and sublimation purification was performed to give 0.8 g of a crystal of Exemplified Compound A10 (47% yield).

The 5% weight loss temperature of the compound was 391° C. and the 10% weight loss temperature thereof was 445° C.

844.4 as M+ of the compound was confirmed by means of Matrix Assisted Laser Desorption/Ionization-Time of Flight Mass Spectrometry (MALDI-TOF MS).

Example 3

Synthesis of Exemplified Compound A34

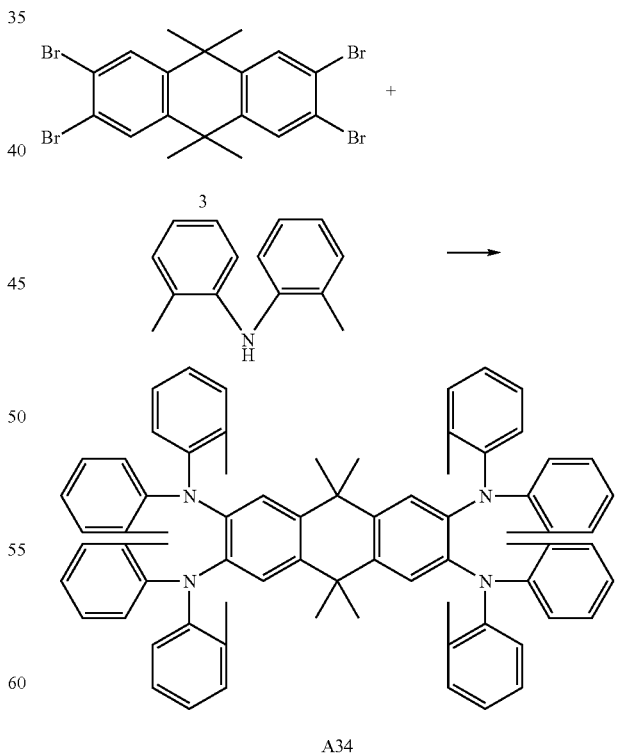

Under nitrogen flow, 1.1 g (2.0 mmol) of the compound (3), 2.0 g (10.0 mmol) of di-o-tolylamine, 2.2 g (23 mmol) of t-butoxy sodium, and 50 mL of o-xylene were placed in a 100 mL three-necked flask. After the solution was heated to 50° C., a solution prepared by dissolving 20 mg of palladium acetate and 80 mg of t-butylphosphine in 4 mL of o-xylene was slowly added dropwise thereto, and the mixture was stirred under heating and reflux for 8 hours. After the completion of the reaction, the reaction liquid was added with water and dried with magnesium sulfate, and the solvent was evaporated under reduced pressure, after which purification by silica gel column chromatography and recrystallization with toluene were performed to give a crystal of Exemplified Compound A34.

Example 4

Synthesis of Exemplified Compound A22

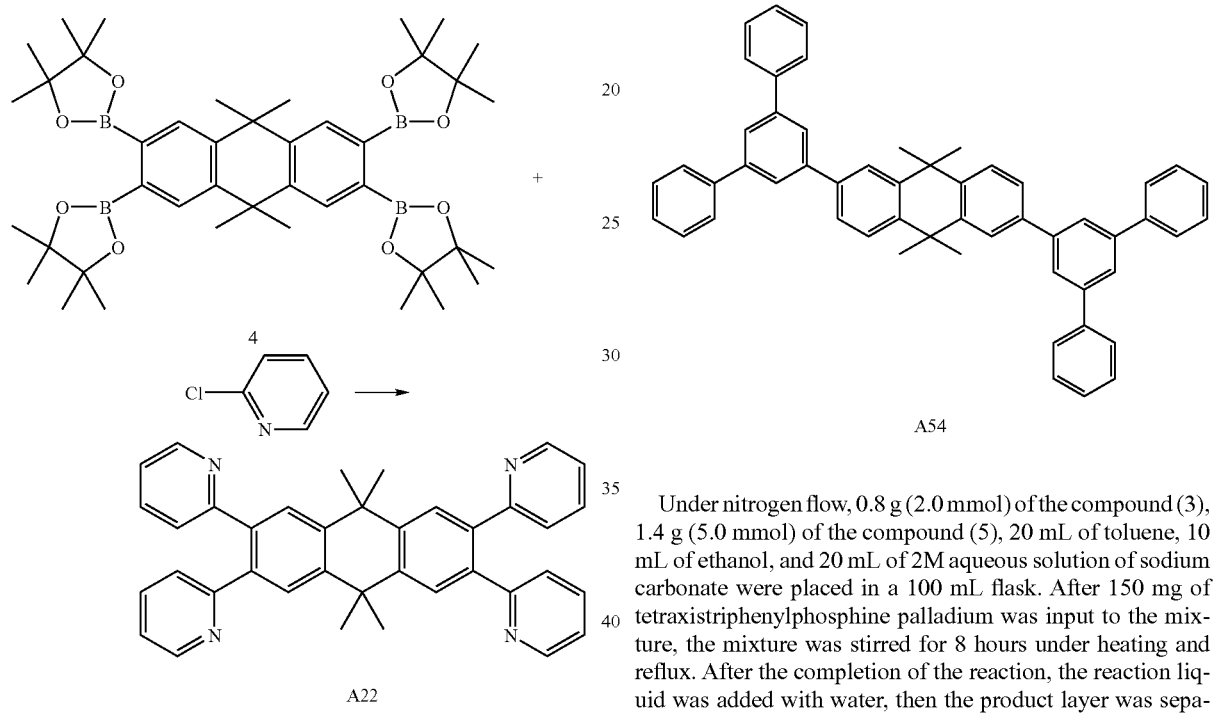

Under nitrogen flow, 1.5 g (2.0 mmol) of the compound (4), 1.1 g (10.0 mmol) of chloropyridine, 20 mL of toluene, 10 mL of ethanol, and 20 mL of 2M aqueous solution of sodium carbonate were placed in a 100 mL flask. After 150 mg of tetraxistriphenylphosphine palladium was input to the mixture, the mixture was stirred for 8 hours under heating and reflux. After the completion of the reaction, the reaction liquid was added with water, then the product layer was separated off, and purification by silica gel chromatography and recrystallization were performed to give a crystal of Exemplified Compound A22.

Example 5

Synthesis of Exemplified Compound A54

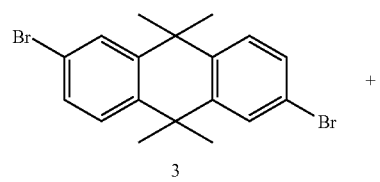

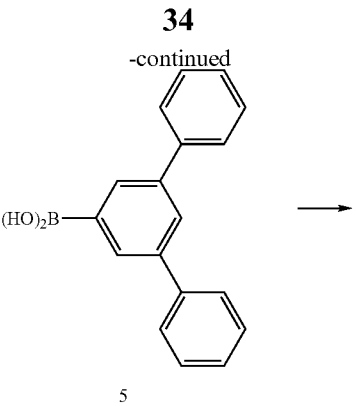

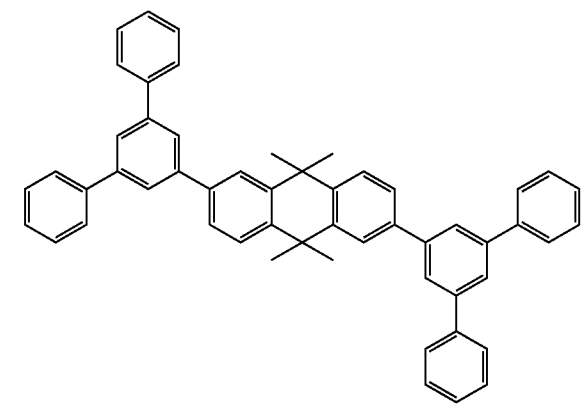

Under nitrogen flow, 0.8 g (2.0 mmol) of the compound (3), 1.4 g (5.0 mmol) of the compound (5), 20 mL of toluene, 10 mL of ethanol, and 20 mL of 2M aqueous solution of sodium carbonate were placed in a 100 mL flask. After 150 mg of tetraxistriphenylphosphine palladium was input to the mixture, the mixture was stirred for 8 hours under heating and reflux. After the completion of the reaction, the reaction liquid was added with water, then the product layer was separated off, and purification by silica gel chromatography and recrystallization were performed to give a crystal of Exemplified Compound A54.

Example 6

In this example, an organic EL device having 3 organic layers such as illustrated in FIG. 1B was produced.

ITO (transparent electrode 14) having a thickness of 100 nm was patterned onto a glass substrate (transparent substrate 15) so as to have an opposing electrode area of 3.14 mm$^2$. The following organic layers and electrode layers were sequentially formed on the ITO substrate through vacuum deposition of the following compounds by using resistive heating in a vacuum chamber of $10^{-4}$ Pa to produce a device.

Hole-transporting layer 13 (40 nm): Compound A

Light-emitting layer 12 (40 nm): Exemplified Compound A1 and Compound B (10% by weight)

Electron-transporting layer 16 (30 nm): Bphen

Metal Electrode Layer 11-1 (15 nm): KF

Metal Electrode Layer 11-2 (100 nm): Al

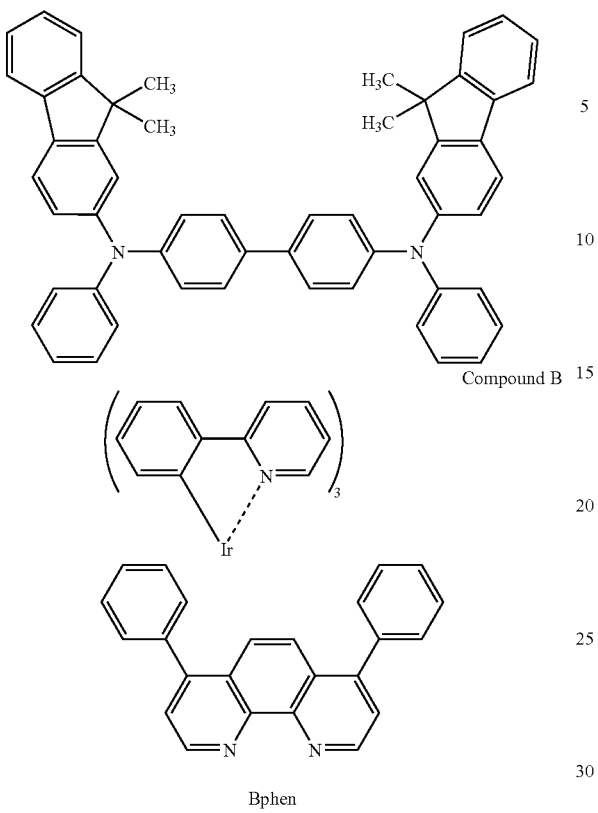

Compound A

Compound B

Bphen

When a voltage was applied to the device, emission of light having the maximum emission wavelength at or near 520 nm was confirmed.

Example 7

An organic EL device was produced by following the same procedure as in Example 6 with the exception that Exemplified Compound A10 was used instead of Exemplified Compound A1. When a voltage was applied to the device, emission of light having the maximum emission wavelength at or near 520 nm was confirmed.

Example 8

An organic EL device was produced by following the same procedure as in Example 6 with the exception that the host material was doubly doped with Compound C (4 wt. %) and Compound D (8 wt. %), not with Compound B. When a voltage was applied to the device, emission of light having the maximum emission wavelength at or near 610 nm was confirmed.

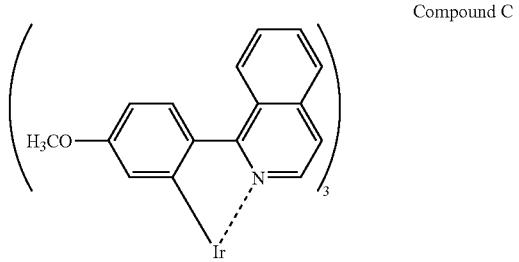

Compound C

Compound D

Example 9

An organic EL device was produced by following the same procedure as in Example 6 with the exception that Compound E was used instead of Compound B. When a voltage was applied to the device, emission of light having the maximum emission wavelength at or near 470 nm was confirmed.

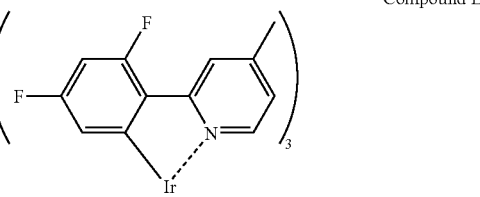

Compound E

Example 10

An organic EL device was produced by following the same procedure as in Example 6 with the exception that Exemplified Compound A10 was used instead of Exemplified Compound A1 and Compound E was used instead of Compound B. When a voltage was applied to the device, emission of light having the maximum emission wavelength at or near 470 nm was confirmed.

Example 11

An organic EL device was produced by following the same procedure as in Example 6 with the exception that Exemplified Compound A10 was used instead of Exemplified Compound A1 and Compound F was used instead of Compound B. When a voltage was applied to the device, emission of light having the maximum emission wavelength at or near 470 nm was confirmed.

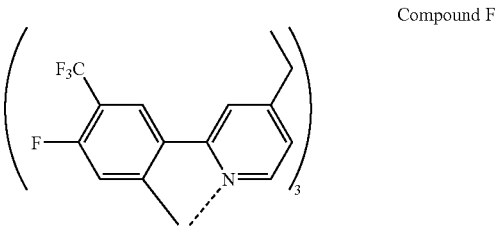

Compound F

Example 12

An organic EL device was produced by following the same procedure as in Example 6 with the exception that Exemplified Compound A54 was used instead of Exemplified Compound A1 and Compound G was used instead of Compound B. When a voltage was applied to the device, emission of light having the maximum emission wavelength at or near 470 nm was confirmed.

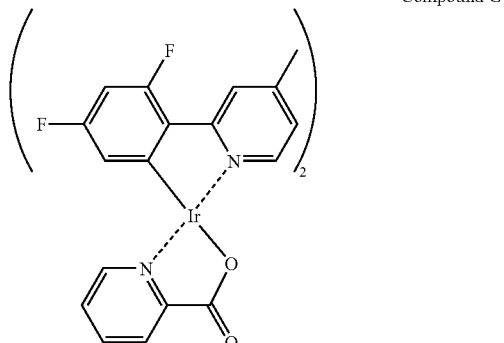

Compound G

Example 13

An organic EL device was produced by following the same procedure as in Example 6 with the exception that the materials of the hole-transporting layer and the light-emitting layer were changed as follows.
Hole-transporting layer (40 nm): Exemplified Compound A34
Light-emitting layer (40 nm): Exemplified Compound A10 and Compound E (10% by weight)
When a voltage was applied to the device, emission of light having the maximum emission wavelength at or near 470 nm was confirmed.

Example 14

An organic EL device was produced by following the same procedure as in Example 6 with the exception that the materials of the light-emitting layer and the electron-transporting layer were changed as follows.
Light-emitting layer (40 nm): Exemplified Compound A10 and Compound E (10% by weight)
Electron-transporting layer (30 nm): Exemplified Compound A22
When a voltage was applied to the device, emission of light having the maximum emission wavelength at or near 470 nm was confirmed.

Example 15

An organic EL device was produced by following the same procedure as in Example 6 with the exception that the materials of the hole-transporting layer and the light-emitting layer were changed as follows.
Hole-transporting layer (40 nm): Exemplified Compound A34
Light-emitting layer (40 nm): Exemplified Compound A18 and Compound E (10% by weight)
When a voltage was applied to the device, emission of light having the maximum emission wavelength at or near 470 nm was confirmed.

Example 16

An organic EL device was produced by following the same procedure as in Example 6 with the exception that the materials of the hole-transporting layer and the light-emitting layer were changed as follows.
Hole-transporting layer (40 nm): Exemplified Compound A75
Light-emitting layer (40 nm): Exemplified Compound A76 and Compound E (10% by weight)
When a voltage was applied to the device, emission of light having the maximum emission wavelength at or near 470 nm was confirmed.

Example 17

In this example, an organic EL device having 3 organic layers such as illustrated in FIG. 1B was produced.
On an ITO substrate prepared by following the same procedure as in Example 6, PEDOT (trade name; manufactured by Bayer; for organic EL use) was coated by spin coating at 1,000 rpm (20 seconds) in a thickness of 40 nm and dried in a vacuum chamber at 120° C. for 1 hour to form a hole-transporting layer 13.
On the hole-transporting layer, a solution of 92 mg of Exemplified Compound A81 and 8 mg of Compound E in 10 g of chlorobenzene was spin-coated at 2,000 rpm for 20 seconds to form an organic layer (light-emitting layer 12) of 50 nm in thickness, and then the film was dried under the same conditions as those in the formation of the hole-transporting layer.
The substrate having the above-mentioned organic layers formed thereon was placed in a vacuum deposition chamber, and Bphen was vacuum vapor deposited thereon in a thickness of 40 nm to prepare an electron-transporting layer 16.
The total thickness of the organic layers was 130 nm.
Next, on the electron-transporting layer, a metal electrode 11 (cathode) having the following constitution was formed.
Metal Electrode Layer 11-1 (15 nm): Al—Li alloy (Li content: 1.8 wt. %)
Metal Electrode Layer 11-2 (100 nm): Al
When a voltage was applied to the device, emission of light having the maximum emission wavelength at or near 470 nm was confirmed.

Example 18

An organic EL device was produced by following the same procedure as in Example 6 with the exception that Exemplified Compound A82 was used instead of Exemplified Compound A81 and Exemplified Compound A22 was used instead of Bphen.

Example 19

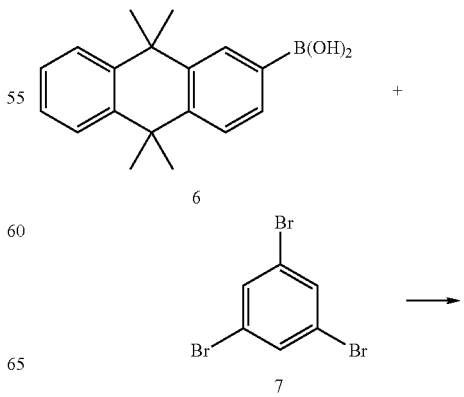

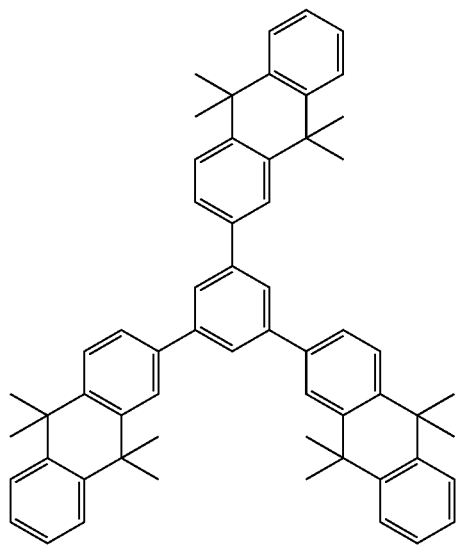

A83

Under nitrogen flow, 0.896 g (3.2 mmol) of the compound (6), 0.31 g (1.0 mmol) of the compound (7), 20 mL of toluene, 10 mL of ethanol, and 20 mL of 2M aqueous solution of sodium carbonate were placed in a 100 mL flask. After 100 mg of tetraxistriphenylphosphine palladium was input to the mixture, the mixture was stirred for 8 hours under heating and reflux. After the completion of the reaction, the reaction liquid was added with water, then the product layer was separated off, and purification by silica gel column chromatography with heptane/toluene mixed solvent, recrystallization, and sublimation purification were performed to give 0.6 g of a crystal of Exemplified Compound A83 (77% yield).

When the compound was dissolved in toluene solution and measured for T1 at 77K, T1 was confirmed with an emission peak of a shortest wavelength at an energy level of 441 nm.

Example 20

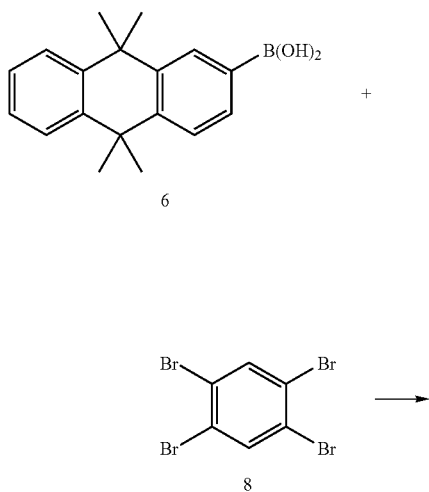

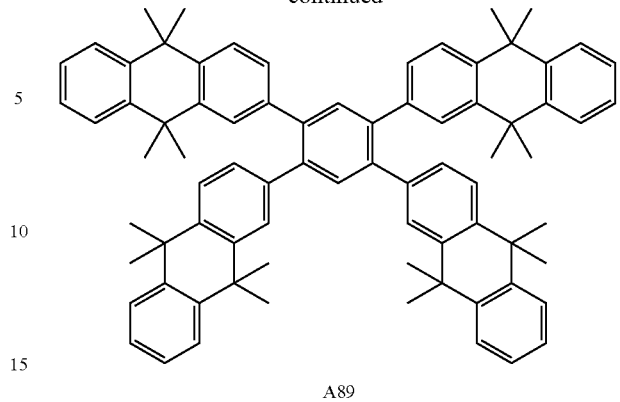

A89

Under nitrogen flow, 1.18 g (4.2 mmol) of the compound (6), 0.39 g (1.0 mmol) of the compound (8), 20 mL of toluene, 10 mL of ethanol, and 20 mL of 2M aqueous solution of sodium carbonate were placed in a 100 mL flask. After 100 mg of tetraxistriphenylphosphine palladium was input to the mixture, the mixture was stirred for 8 hours under heating and reflux. After the completion of the reaction, the reaction liquid was added with water, then the product layer was separated off, and purification by silica gel column chromatography with heptane/toluene mixed solvent, recrystallization, and sublimation purification were performed to give 0.71 g of a crystal of Exemplified Compound A89 (70% yield).

When a voltage was applied to an organic EL device produced using the above prepared compound by the same procedure as described in Example 6, emission of light having the maximum emission wavelength at or near 470 nm was confirmed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-185488, filed on Jul. 5, 2006, which is hereby incorporated by reference herein in its entirety.

What is claimed is:

1. A compound for an organic EL device having a structure represented by the general formula (2):

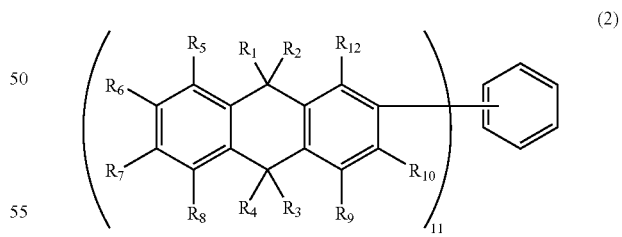

(2)

wherein $R_1$, $R_2$, $R_3$, and $R_4$ each represent, independently of one another, a halogen atom, a linear or branched alkyl group having 1 to 20 carbon atoms in which one methylene group or at least two non-adjacent methylene groups of the alkyl group may be replaced by —O—, —S—, —CO—, —CO—O—, —O—CO—, —CH=CH—, or —C≡C—, at least one methylene group of the alkyl group may be replaced by an arylene group which may have a substituent or by a divalent heterocyclic group which may have a substituent, and hydrogen atom(s) of the alkyl group may be substituted with fluorine atom(s), an amino group which may have a substituent, a silyl group which may have a substituent, an aryl group which may have a substituent, or a heterocyclic group which may have a substituent;

$R_5$, $R_6$, $R_7$, $R_8$, $R_9$, $R_{10}$, and $R_{12}$ each represent, independently of one another, a hydrogen atom, a halogen atom, a linear or branched alkyl group having 1 to 20 carbon atoms in which one methylene group or at least two non-adjacent methylene groups of the alkyl group may be replaced by —O—, —S—, —CO—, —CO—O—, —O—CO—, —CH=CH—, or —C≡C—, at least one methylene group of the alkyl group may be replaced by an arylene group which may have a substituent or by a divalent heterocyclic group which may have a substituent, and hydrogen atom(s) of the alkyl group may be substituted with fluorine atom(s), an amino group which may have a substituent, a silyl group which may have a substituent, a phenyl, naphthyl, pyrenyl, fluorenyl, phenanthrenyl, chrysenyl, fluoranthenyl, triphenylenyl, tetraphenylanthracenyl group which may have a substituent, or a heterocyclic group which may have a substituent, and adjacent ones of $R_5$, $R_6$, $R_7$, $R_8$, $R_9$, $R_{10}$, $R_{11}$, and $R_{12}$ may be joined to form a ring structure;

n represents an integer of 2 to 6.

2. The compound according to claim 1, wherein $R_1$, $R_2$, $R_3$, and $R_4$ each represent an alkyl group.

3. An organic EL device comprising an anode, a cathode, and an organic compound layer disposed between the anode and the cathode, wherein the organic compound layer comprises the compound set forth in claim 1.

4. The organic EL device according to claim 3, wherein the organic compound layer is a light-emitting layer.

5. The organic EL device according to claim 4, wherein the light-emitting layer comprises a phosphorescent material.

6. The organic EL device according to claim 5, wherein the phosphorescent material is a metal coordination compound.

7. The organic EL device according to claim 6, wherein the metal coordination compound is an Iridium coordination compound.

8. The organic EL device according to claim 4, wherein the light-emitting layer comprises a plurality of kinds of phosphorescent materials.

9. The organic EL device according to claim 3, wherein the organic compound layer is a hole-transporting layer or an electron-transporting layer.

10. An image display apparatus comprising:
the organic EL device set forth in claim 3; and
a unit for supplying an electrical signal to the organic EL device.

* * * * *